(12) United States Patent
Hattori et al.

(10) Patent No.: US 6,933,364 B1
(45) Date of Patent: Aug. 23, 2005

(54) SECRETORY THYROID STIMULATING HORMONE RECEPTOR, AND METHOD FOR ASSAYING ANTI-THYROID STIMULATING HORMONE RECEPTOR ANTIBODY USING THE SAME

(75) Inventors: Yoshiyuki Hattori, Kyoto (JP); Takashi Akamizu, Kyoto (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/644,858

(22) Filed: Aug. 24, 2000

(30) Foreign Application Priority Data

Aug. 24, 1999 (JP) ........................................ P. 11-236983
Feb. 10, 2000 (JP) .................................... P. 2000-038214

(51) Int. Cl.$^7$ ........................ C07K 14/705; C12N 15/62
(52) U.S. Cl. ...................... 530/350; 435/69.1; 435/69.7; 536/23.4
(58) Field of Search .............................. 435/69.1, 69.7; 530/350; 536/23.4

(56) References Cited

U.S. PATENT DOCUMENTS

| | | | |
|---|---|---|---|
| 5,144,007 A | 9/1992 | Pfahl | 530/350 |
| 5,438,126 A | 8/1995 | DeGroot et al. | 536/23.5 |
| 5,925,549 A | * 7/1999 | Hsueh et al. | 435/69.7 |

OTHER PUBLICATIONS

Rapoport, B., et al. (1998) "The Thyrotropin (TSH) Receptor: Interaction with TSH and Autoantibodies" Endocrine Reviews, 19;(6): 673–716.

Kosugi, S., et al. (1997) "Epitope Analysis of the Thyrotropin Receptor" Molecular and Cellular Endocrinology, 128: 11–18.

Dallas, J., et al. (1996) "Thyrotropin (TSH) Receptor Antibodies (TSHrAb) Can Inhibit TSH–Mediated Cyclic Adenosine 3', 5'–Monophosphate Production in Thyroid Cells by Either Blocking TSH Binding or Affecting a Step Subsequent to TSH Binding" Endocrinology, 137(8): 3329–3339.

Seetharamaiah et al, Journal of Immunology, vol. 158, "Require– of Glycosylation of the Human . . . ", pp. 2798–2804, 1997.

Park et al, Molecular and Cellular Endocrinology, vol. 147, "Different bioactivities of human . . . ", pp. 133–142, 1999.

Patibandla et la, ENDOCRINOLOGY, vol. 138, No. 4, "Differential Reactivities of Recombinant . . . ", pp. 1559–1566, 1997.

Chazenbalk et al, Journal of Biological Chemistry, vol. 272, No. 30, "Engineering the Human . . . ", pp. 18959–18965, Jul. 25, 1997.

Seetharamaiah et al, AUTOIMMUNITY, vol. 14, "Induction of TSH Binding Inhibitory Immunoglobulins . . . ", pp. 315–320, 1993.

Vlase et al, ENDOCRINOLOGY, vol. 138, No. 4, "Folding–Dependent Binding of Thyrotropin (TSH) . . . ", pp. 1658–1666, 1997.

Huang et al, Journal of Molecular Endoctrinology, vol. 10, "The thyrotrophin hormone receptor of Graves . . . ", pp. 127–142, 1993.

Smith et al, Endocrine Reviews, vol. 9, No. 1, "Autoantibodies to the Thyrotropin Receptor", pp. 106–121, 1988.

Chazenbalk et al, Journal of Biological Chemistry, vol. 270, No. 4, "Expression of the Extracellular . . . ", pp. 1543–1549, 1994.

* cited by examiner

*Primary Examiner*—John Ulm
(74) *Attorney, Agent, or Firm*—Jacobson Holman PLLC

(57) ABSTRACT

A recombinant soluble human thyroid hormone receptor, comprising an extracellular domain moiety of a human thyroid hormone receptor, or a mutant thereof, being secretory, and having reactivity with an anti-human thyroid stimulating hormone receptor autoantibody; a composition for assaying an anti-human thyroid stimulating hormone receptor antibody, comprising the receptor and a carrier or diluent; a method for assaying an anti-human thyroid stimulating hormone receptor antibody, comprising reacting an anti-human thyroid stimulating hormone receptor antibody with the receptor; and a process for producing a recombinant soluble human thyroid hormone receptor which is secretory and has reactivity with an anti-human thyroid stimulating hormone receptor autoantibody, comprising infecting an insect cell with a recombinant *baculovirus* introduced with an extracellular domain moiety of a gene encoding a human thyroid hormone receptor or a mutant thereof, and culturing the infected cell.

5 Claims, 16 Drawing Sheets

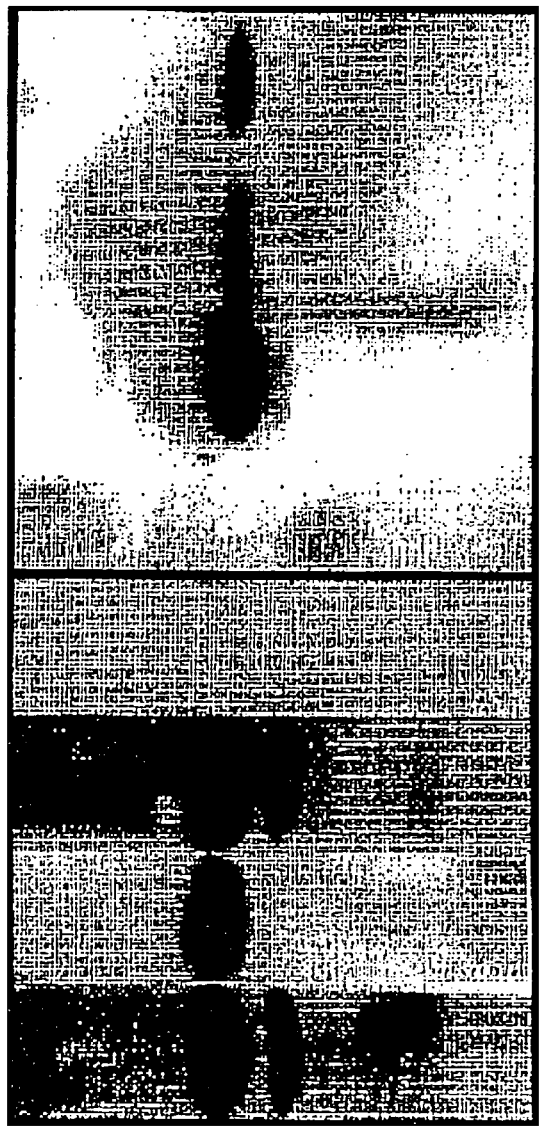

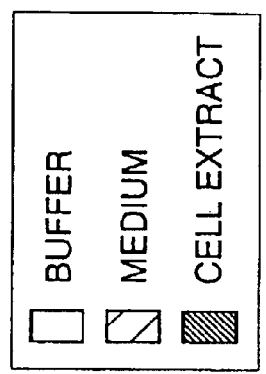
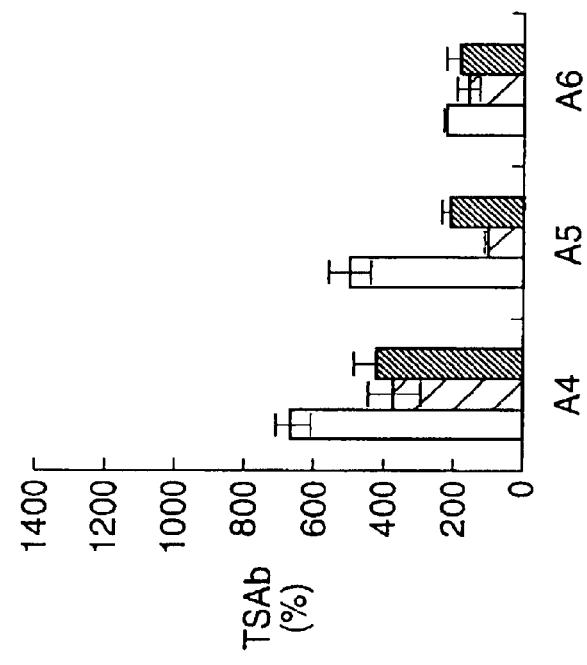
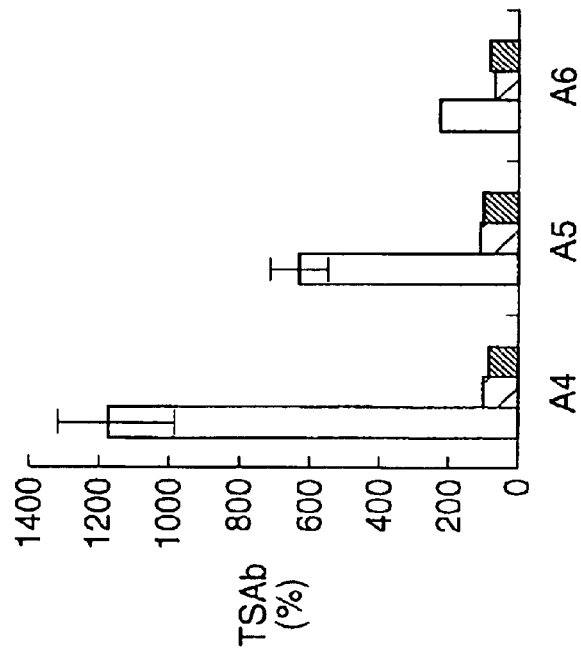

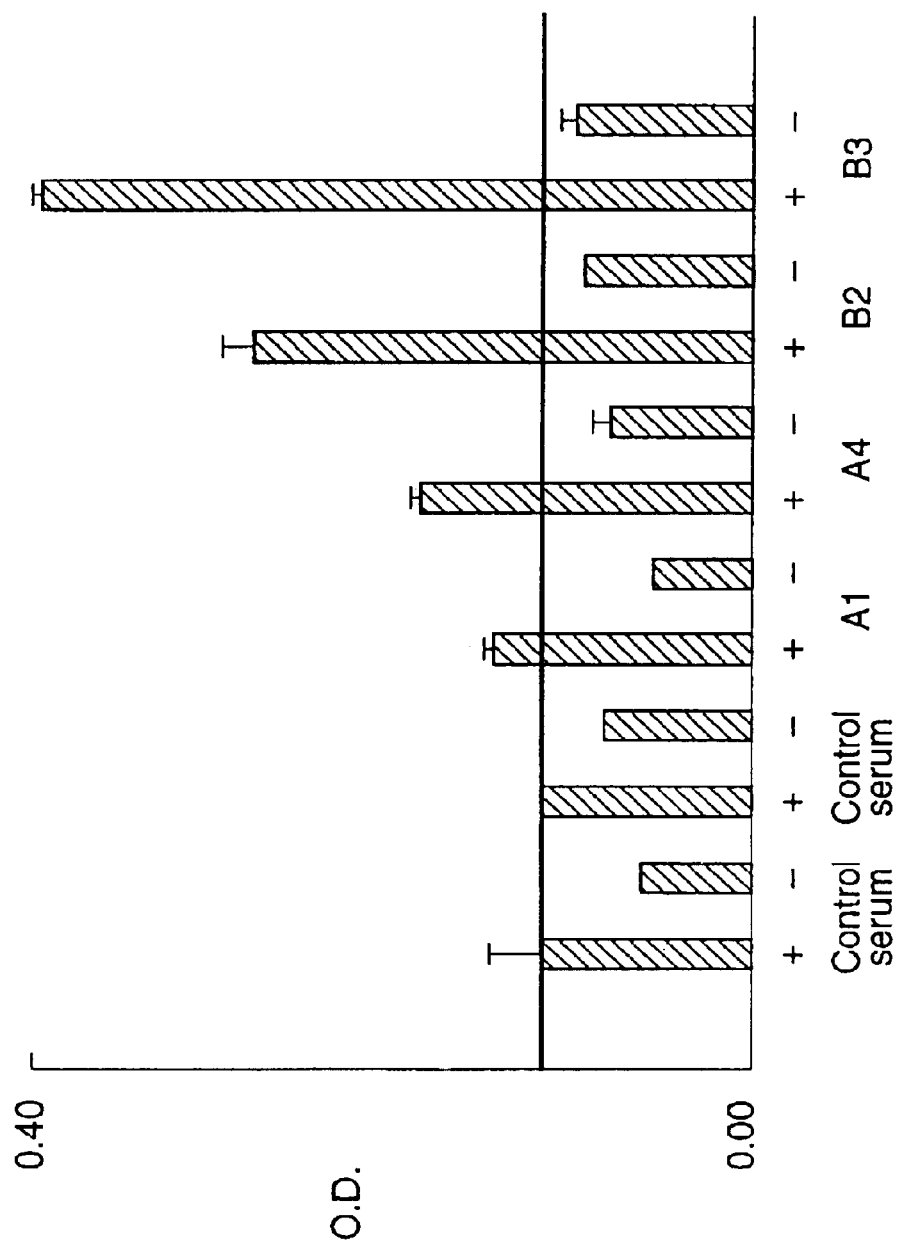

SEQUENCE LISTING

```
<160> NUMBER OF SEQ ID NOS:   25

<210> SEQ ID NO 1
<211> LENGTH: 32
<212> TYPE: DNA
<213> ORGANISM: Artificial/Unknown
<220> FEATURE:
<221> NAME/KEY: misc_feature
<222> LOCATION: ()..()
<223> OTHER INFORMATION: sense primer shTSHR-1

<400> SEQUENCE: 1
caagaattca ccatgaggcc ggcggacttg ct                              32

<210> SEQ ID NO 2
<211> LENGTH: 32
<212> TYPE: DNA
<213> ORGANISM: Artificial/Unknown
<220> FEATURE:
<221> NAME/KEY: misc_feature
<222> LOCATION: ()..()
```

<223> OTHER INFORMATION: antisense primer ahTSHR-1

<400> SEQUENCE: 2
ccagatatct tcacacgggt tgaactcatc gg            32

<210> SEQ ID NO 3
<211> LENGTH: 26
<212> TYPE: DNA
<213> ORGANISM: Artificial/Unknown
<220> FEATURE:
<221> NAME/KEY: misc_feature
<222> LOCATION: ()..()
<223> OTHER INFORMATION: oligonucleotide

<400> SEQUENCE: 3
cctcatcatc atcatcatca ttaagc                  26

<210> SEQ ID NO 4
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: oligonucleotide

<400> SEQUENCE: 4
ggccgcttaa tgatgatgat gatgatgagg              30

<210> SEQ ID NO 5
<211> LENGTH: 417
<212> TYPE: PRT
<213> ORGANISM: Artificial/Unknown
<220> FEATURE:
<221> NAME/KEY: misc_feature
<222> LOCATION: ()..()
<223> OTHER INFORMATION: recombinant tranfer vector sTSHR

<400> SEQUENCE: 5

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
                20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

-continued

```
Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
            195                 200                 205

Lys Asn Lys Tyr Leu Thr Val Ile Asp Lys Asp Ala Phe Gly Gly Val
210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
            355                 360                 365

Glu Leu Lys Asn Pro Gln Glu Glu Thr Leu Gln Ala Phe Asp Ser His
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Pro His His His His
                405                 410                 415

His

<210> SEQ ID NO 6
<211> LENGTH: 34
<212> TYPE: DNA
<213> ORGANISM: Artificial/Unknown
<220> FEATURE:
<221> NAME/KEY: misc_feature
<222> LOCATION: ()..()
<223> OTHER INFORMATION: sense primer shTSHR-2

<400> SEQUENCE: 6
tgctgcggcc gcagctgaag aacaagagga tgag                              34

<210> SEQ ID NO 7
<211> LENGTH: 34
<212> TYPE: DNA
<213> ORGANISM: Artificial/Unknown
<220> FEATURE:
<221> NAME/KEY: misc_feature
<222> LOCATION: ()..()
<223> OTHER INFORMATION: antisense primer ahTSHR-2

<400> SEQUENCE: 7
cagctgcggc cgcagcatga gcgttgttat gagt                              34

<210> SEQ ID NO 8
<211> LENGTH: 417
<212> TYPE: PRT
```

-continued

```
<213> ORGANISM: Artificial/Unknown
<220> FEATURE:
<221> NAME/KEY: misc_feature
<222> LOCATION: ()..()
<223> OTHER INFORMATION: sTSHR

<400> SEQUENCE: 8
```

Met Arg Pro Ala Asp Leu Leu Gln Leu Val Leu Leu Asp Leu Pro
1               5                   10                  15

Arg Asp Leu Gly Gly Met Gly Cys Ser Ser Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Ala
            340                 345                 350

Ala Ala Ala Ala Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Pro His His His His
                405                 410                 415

His

<210> SEQ ID NO 9
<211> LENGTH: 32
<212> TYPE: DNA
<213> ORGANISM: Artificial/Unknown
<220> FEATURE:
<221> NAME/KEY: misc_feature
<222> LOCATION: ()..()
<223> OTHER INFORMATION: sense primer shTSHR-3

<400> SEQUENCE: 9
gcattgttgg gtacggccag gagctcaaaa ac                              32

<210> SEQ ID NO 10
<211> LENGTH: 32
<212> TYPE: DNA
<213> ORGANISM: Artificial/Unknown
<220> FEATURE:
<221> NAME/KEY: misc_feature
<222> LOCATION: ()..()
<223> OTHER INFORMATION: antisense primer ahTSHR-3

<400> SEQUENCE: 10
ttgagctcct ggccgtaccc aacaatgctg tc                              32

<210> SEQ ID NO 11
<211> LENGTH: 388
<212> TYPE: PRT
<213> ORGANISM: Artificial/Unknown
<220> FEATURE:
<221> NAME/KEY: misc_feature
<222> LOCATION: ()..()
<223> OTHER INFORMATION: sTSHR

<400> SEQUENCE: 11

Met Arg Pro Ala Asp Leu Leu Gln Leu Val Leu Leu Asp Leu Pro
1               5                   10                  15

Arg Asp Leu Gly Gly Met Gly Cys Ser Ser Pro Pro Cys Glu Cys His
                20                  25                  30

Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

```
Asn Pro Tyr Met Thr Ser Ile Pro Val Asn Ala Phe Gln Gly Leu Cys
            165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
            195                 200                 205

Lys Asn Lys Tyr Leu Thr Val Ile Asp Lys Asp Ala Phe Gly Gly Val
210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
            245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
            290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
            325                 330                 335

Tyr Gly Gln Glu Leu Lys Asn Pro Gln Glu Glu Thr Leu Gln Ala Phe
            340                 345                 350

Asp Ser His Tyr Asp Tyr Thr Ile Cys Gly Asp Ser Glu Asp Met Val
            355                 360                 365

Cys Thr Pro Lys Ser Asp Glu Phe Asn Pro Cys Glu Asp Pro His His
            370                 375                 380

His His His His
385

<210> SEQ ID NO 12
<211> LENGTH: 20
<212> TYPE: DNA
<213> ORGANISM: Artificial/Unknown
<220> FEATURE:
<221> NAME/KEY: misc_feature
<222> LOCATION: ()..()
<223> OTHER INFORMATION: antisense primer ahTSHR-4

<400> SEQUENCE: 12
cttgtagccc attatgtctt                                              20

<210> SEQ ID NO 13
<211> LENGTH: 422
<212> TYPE: PRT
<213> ORGANISM: Artificial/Unknown
<220> FEATURE:
<221> NAME/KEY: misc_feature
<222> LOCATION: ()..()
<223> OTHER INFORMATION: transfer vector with cDNA encoding sTSHR

<400> SEQUENCE: 13

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
            35                  40                  45
```

```
Ser Leu Pro Pro Ser Thr Gln Thr Leu Lys Leu Ile Glu Thr His Leu
 50                  55                  60

Arg Thr Ile Pro Ser His Ala Phe Ser Asn Leu Pro Asn Ile Ser Arg
 65                      70                  75                  80

Ile Tyr Val Ser Ile Asp Val Thr Leu Gln Gln Leu Glu Ser His Ser
                 85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Pro
                405                 410                 415

His His His His His His
            420

<210> SEQ ID NO 14
<211> LENGTH: 29
<212> TYPE: DNA
<213> ORGANISM: Artificial/Unknown
<220> FEATURE:
```

```
<221> NAME/KEY: misc_feature
<222> LOCATION: ()..()
<223> OTHER INFORMATION: sense primer shTSHR-4

<400> SEQUENCE: 14
caagaattcg gaatgggtg ttcgtctcc                                              29

<210> SEQ ID NO 15
<211> LENGTH: 32
<212> TYPE: DNA
<213> ORGANISM: Artificial/Unknown
<220> FEATURE:
<221> NAME/KEY: misc_feature
<222> LOCATION: ()..()
<223> OTHER INFORMATION: sense primer sGP

<400> SEQUENCE: 15
ccaggatcca ccatgctact agtaaatcag tc                                         32

<210> SEQ ID NO 16
<211> LENGTH: 29
<212> TYPE: DNA
<213> ORGANISM: Artificial/Unknown
<220> FEATURE:
<221> NAME/KEY: misc_feature
<222> LOCATION: ()..()
<223> OTHER INFORMATION: antisense primer aGP

<400> SEQUENCE: 16
caagaattca tccgccgcaa aggcagaat                                             29

<210> SEQ ID NO 17
<211> LENGTH: 439
<212> TYPE: PRT
<213> ORGANISM: Artificial/Unknown
<220> FEATURE:
<221> NAME/KEY: misc_feature
<222> LOCATION: ()..()
<223> OTHER INFORMATION: sTSHR

<400> SEQUENCE: 17
```

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Glu Phe Gly Met Gly Cys Ser Ser
        35                  40                  45

Pro Pro Cys Glu Cys His Gln Glu Glu Asp Phe Arg Val Thr Cys Lys
    50                  55                  60

Asp Ile Gln Arg Ile Pro Ser Leu Pro Pro Ser Thr Gln Thr Leu Lys
65                  70                  75                  80

Leu Ile Glu Thr His Leu Arg Thr Ile Pro Ser His Ala Phe Ser Asn
                85                  90                  95

Leu Pro Asn Ile Ser Arg Ile Tyr Val Ser Ile Asp Val Thr Leu Gln
            100                 105                 110

Gln Leu Glu Ser His Ser Phe Tyr Asn Leu Ser Lys Val Thr His Ile
        115                 120                 125

Glu Ile Arg Asn Thr Arg Asn Leu Thr Tyr Ile Asp Pro Asp Ala Leu
    130                 135                 140

Lys Glu Leu Pro Leu Leu Lys Phe Leu Gly Ile Phe Asn Thr Gly Leu
145                 150                 155                 160

Lys Met Phe Pro Asp Leu Thr Lys Val Tyr Ser Thr Asp Ile Phe Phe

-continued

```
                165                 170                 175
Ile Leu Glu Ile Thr Asp Asn Pro Tyr Met Thr Ser Ile Pro Val Asn
            180                 185                 190
Ala Phe Gln Gly Leu Cys Asn Glu Thr Leu Thr Leu Lys Leu Tyr Asn
            195                 200                 205
Asn Gly Phe Thr Ser Val Gln Gly Tyr Ala Phe Asn Gly Thr Lys Leu
            210                 215                 220
Asp Ala Val Tyr Leu Asn Lys Asn Lys Tyr Leu Thr Val Ile Asp Lys
225                 230                 235                 240
Asp Ala Phe Gly Gly Val Tyr Ser Gly Pro Ser Leu Leu Asp Val Ser
            245                 250                 255
Gln Thr Ser Val Thr Ala Leu Pro Ser Lys Gly Leu Glu His Leu Lys
            260                 265                 270
Glu Leu Ile Ala Arg Asn Thr Trp Thr Leu Lys Lys Leu Pro Leu Ser
            275                 280                 285
Leu Ser Phe Leu His Leu Thr Arg Ala Asp Leu Ser Tyr Pro Ser His
            290                 295                 300
Cys Cys Ala Phe Lys Asn Gln Lys Lys Ile Arg Gly Ile Leu Glu Ser
305                 310                 315                 320
Leu Met Cys Asn Glu Ser Ser Met Gln Ser Leu Arg Gln Arg Lys Ser
            325                 330                 335
Val Asn Ala Leu Asn Ser Pro Leu His Gln Glu Tyr Glu Glu Asn Leu
            340                 345                 350
Gly Asp Ser Ile Val Gly Tyr Lys Glu Lys Ser Lys Phe Gln Asp Thr
            355                 360                 365
His Asn Asn Ala His Tyr Tyr Val Phe Phe Glu Glu Gln Glu Asp Glu
            370                 375                 380
Ile Ile Gly Phe Gly Gln Glu Leu Lys Asn Pro Gln Glu Glu Thr Leu
385                 390                 395                 400
Gln Ala Phe Asp Ser His Tyr Asp Tyr Thr Ile Cys Gly Asp Ser Glu
            405                 410                 415
Asp Met Val Cys Thr Pro Lys Ser Asp Glu Phe Asn Pro Cys Glu Asp
            420                 425                 430
Pro His His His His His His
            435
```

```
<210> SEQ ID NO 18
<211> LENGTH: 444
<212> TYPE: PRT
<213> ORGANISM: Artificial/Unknown
<220> FEATURE:
<221> NAME/KEY: misc_feature
<222> LOCATION: ()..()
<223> OTHER INFORMATION: sTSHR

<400> SEQUENCE: 18

Met Leu Leu Val Asn Gln Ser His Gln Gly Phe Asn Lys Glu His Thr
1               5                   10                  15
Ser Lys Met Val Ser Ala Ile Val Leu Tyr Val Leu Leu Ala Ala Ala
            20                  25                  30
Ala His Ser Ala Phe Ala Ala Asp Glu Phe Gly Met Gly Cys Ser Ser
            35                  40                  45
Pro Pro Cys Glu Cys His Gln Glu Glu Asp Phe Arg Val Thr Cys Lys
            50                  55                  60
Asp Ile Gln Arg Ile Pro Ser Leu Pro Pro Ser Thr Gln Thr Leu Lys
65                  70                  75                  80
```

```
Leu Ile Glu Thr His Leu Arg Thr Ile Pro Ser His Ala Phe Ser Asn
                 85                  90                  95

Leu Pro Asn Ile Ser Arg Ile Tyr Val Ser Ile Asp Val Thr Leu Gln
            100                 105                 110

Gln Leu Glu Ser His Ser Phe Tyr Asn Leu Ser Lys Val Thr His Ile
        115                 120                 125

Glu Ile Arg Asn Thr Arg Asn Leu Thr Tyr Ile Asp Pro Asp Ala Leu
    130                 135                 140

Lys Glu Leu Pro Leu Leu Lys Phe Leu Gly Ile Phe Asn Thr Gly Leu
145                 150                 155                 160

Lys Met Phe Pro Asp Leu Thr Lys Val Tyr Ser Thr Asp Ile Phe Phe
                165                 170                 175

Ile Leu Glu Ile Thr Asp Asn Pro Tyr Met Thr Ser Ile Pro Val Asn
            180                 185                 190

Ala Phe Gln Gly Leu Cys Asn Glu Thr Leu Thr Leu Lys Leu Tyr Asn
        195                 200                 205

Asn Gly Phe Thr Ser Val Gln Gly Tyr Ala Phe Asn Gly Thr Lys Leu
    210                 215                 220

Asp Ala Val Tyr Leu Asn Lys Asn Lys Tyr Leu Thr Val Ile Asp Lys
225                 230                 235                 240

Asp Ala Phe Gly Gly Val Tyr Ser Gly Pro Ser Leu Leu Asp Val Ser
                245                 250                 255

Gln Thr Ser Val Thr Ala Leu Pro Ser Lys Gly Leu Glu His Leu Lys
            260                 265                 270

Glu Leu Ile Ala Arg Asn Thr Trp Thr Leu Lys Lys Leu Pro Leu Ser
        275                 280                 285

Leu Ser Phe Leu His Leu Thr Arg Ala Asp Leu Ser Tyr Pro Ser His
    290                 295                 300

Cys Cys Ala Phe Lys Asn Gln Lys Lys Ile Arg Gly Ile Leu Glu Ser
305                 310                 315                 320

Leu Met Cys Asn Glu Ser Ser Met Gln Ser Leu Arg Gln Arg Lys Ser
                325                 330                 335

Val Asn Ala Leu Asn Ser Pro Leu His Gln Glu Tyr Glu Glu Asn Leu
            340                 345                 350

Gly Asp Ser Ile Val Gly Tyr Lys Glu Lys Ser Lys Phe Gln Asp Thr
        355                 360                 365

His Asn Asn Ala His Tyr Tyr Val Phe Phe Glu Glu Gln Glu Asp Glu
    370                 375                 380

Ile Ile Gly Phe Gly Gln Glu Leu Lys Asn Pro Gln Glu Glu Thr Leu
385                 390                 395                 400

Gln Ala Phe Asp Ser His Tyr Asp Tyr Thr Ile Cys Gly Asp Ser Glu
                405                 410                 415

Asp Met Val Cys Thr Pro Lys Ser Asp Glu Phe Asn Pro Cys Glu Asp
            420                 425                 430

Ile Met Gly Tyr Lys Pro His His His His His
        435                 440

<210> SEQ ID NO 19
<211> LENGTH: 42
<212> TYPE: PRT
<213> ORGANISM: Baculovirus
<220> FEATURE:
<221> NAME/KEY: SIGNAL
<222> LOCATION: (1)..(42)
<223> OTHER INFORMATION: 42 Amino acid residues containing a signal
```

-continued peptide of baculovirus

<400> SEQUENCE: 19

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Glu Phe
            35                  40

<210> SEQ ID NO 20
<211> LENGTH: 1254
<212> TYPE: DNA
<213> ORGANISM: Artificial/Unknown
<220> FEATURE:
<221> NAME/KEY: CDS
<222> LOCATION: (1)..(1254)
<223> OTHER INFORMATION: sTSHR

<400> SEQUENCE: 20

| atg agg ccg gcg gac ttg ctg cag ctg gtg ctg ctc gac ctg ccc | 48 |
| Met Arg Pro Ala Asp Leu Leu Gln Leu Val Leu Leu Asp Leu Pro | |
| 1               5                   10                  15 | |

| agg gac ctg ggc gga atg ggg tgt tcg tct cca ccc tgc gag tgc cat | 96 |
| Arg Asp Leu Gly Gly Met Gly Cys Ser Ser Pro Pro Cys Glu Cys His | |
|             20                  25                  30 | |

| cag gag gag gac ttc aga gtc acc tgc aag gat att caa cgc atc ccc | 144 |
| Gln Glu Glu Asp Phe Arg Val Thr Cys Lys Asp Ile Gln Arg Ile Pro | |
|         35                  40                  45 | |

| agc tta ccg ccc agt acg cag act ctg aag ctt att gag act cac ctg | 192 |
| Ser Leu Pro Pro Ser Thr Gln Thr Leu Lys Leu Ile Glu Thr His Leu | |
|     50                  55                  60 | |

| aga act att cca agt cat gca ttt tct aat ctg ccc aat att tcc aga | 240 |
| Arg Thr Ile Pro Ser His Ala Phe Ser Asn Leu Pro Asn Ile Ser Arg | |
| 65                  70                  75                  80 | |

| atc tac gta tct ata gat gtg act ctg cag cag ctg gaa tca cac tcc | 288 |
| Ile Tyr Val Ser Ile Asp Val Thr Leu Gln Gln Leu Glu Ser His Ser | |
|                 85                  90                  95 | |

| ttc tac aat ttg agt aaa gtg act cac ata gaa att cgg aat acc agg | 336 |
| Phe Tyr Asn Leu Ser Lys Val Thr His Ile Glu Ile Arg Asn Thr Arg | |
|             100                 105                 110 | |

| aac tta act tac ata gac cct gat gcc ctc aaa gag ctc ccc ctc cta | 384 |
| Asn Leu Thr Tyr Ile Asp Pro Asp Ala Leu Lys Glu Leu Pro Leu Leu | |
|         115                 120                 125 | |

| aag ttc ctt ggc att ttc aac act gga ctt aaa atg ttc cct gac ctg | 432 |
| Lys Phe Leu Gly Ile Phe Asn Thr Gly Leu Lys Met Phe Pro Asp Leu | |
|     130                 135                 140 | |

| acc aaa gtt tat tcc act gat ata ttc ttt ata ctt gaa att aca gac | 480 |
| Thr Lys Val Tyr Ser Thr Asp Ile Phe Phe Ile Leu Glu Ile Thr Asp | |
| 145                 150                 155                 160 | |

| aac cct tac atg acg tca atc cct gtg aat gct ttt cag gga cta tgc | 528 |
| Asn Pro Tyr Met Thr Ser Ile Pro Val Asn Ala Phe Gln Gly Leu Cys | |
|                 165                 170                 175 | |

| aat gaa acc ttg aca ctg aag ctg tac aac aac ggc ttt act tca gtc | 576 |
| Asn Glu Thr Leu Thr Leu Lys Leu Tyr Asn Asn Gly Phe Thr Ser Val | |
|             180                 185                 190 | |

| caa gga tat gct ttc aat ggg aca aag ctg gat gct gtt tac cta aac | 624 |
| Gln Gly Tyr Ala Phe Asn Gly Thr Lys Leu Asp Ala Val Tyr Leu Asn | |
|         195                 200                 205 | |

| aag aat aaa tac ctg aca gtt att gac aaa gat gca ttt gga gga gta | 672 |
| Lys Asn Lys Tyr Leu Thr Val Ile Asp Lys Asp Ala Phe Gly Gly Val | |

-continued

```
                  210                 215                 220
tac agt gga cca agc ttg ctg gac gtg tct caa acc agt gtc act gcc        720
Tyr Ser Gly Pro Ser Leu Leu Asp Val Ser Gln Thr Ser Val Thr Ala
225                 230                 235                 240 ctt cca tcc aaa ggc ctg gag cac ctg aag gaa ctg ata gca aga aac        768
Leu Pro Ser Lys Gly Leu Glu His Leu Lys Glu Leu Ile Ala Arg Asn
                245                 250                 255 acc tgg act ctt aag aaa ctt cca ctt tcc ttg agt ttc ctt cac ctc        816
Thr Trp Thr Leu Lys Lys Leu Pro Leu Ser Leu Ser Phe Leu His Leu
            260                 265                 270 aca cgg gct gac ctt tct tac cca agc cac tgc tgt gcc ttt aag aat        864
Thr Arg Ala Asp Leu Ser Tyr Pro Ser His Cys Cys Ala Phe Lys Asn
        275                 280                 285 cag aag aaa atc aga gga atc ctt gag tcc ttg atg tgt aat gag agc        912
Gln Lys Lys Ile Arg Gly Ile Leu Glu Ser Leu Met Cys Asn Glu Ser
    290                 295                 300 agt atg cag agc ttg cgc cag aga aaa tct gtg aat gcc ttg aat agc        960
Ser Met Gln Ser Leu Arg Gln Arg Lys Ser Val Asn Ala Leu Asn Ser
305                 310                 315                 320 ccc ctc cac cag gaa tat gaa gag aat ctg ggt gac agc att gtt ggg       1008
Pro Leu His Gln Glu Tyr Glu Glu Asn Leu Gly Asp Ser Ile Val Gly
                325                 330                 335 tac aag gaa aag tcc aag ttc cag gat act cat aac aac gct cat tat       1056
Tyr Lys Glu Lys Ser Lys Phe Gln Asp Thr His Asn Asn Ala His Tyr
            340                 345                 350 tac gtc ttc ttt gaa gaa caa gag gat gag atc att ggt ttt ggc cag       1104
Tyr Val Phe Phe Glu Glu Gln Glu Asp Glu Ile Ile Gly Phe Gly Gln
        355                 360                 365 gag ctc aaa aac ccc cag gaa gag act cta caa gct ttt gac agc cat       1152
Glu Leu Lys Asn Pro Gln Glu Glu Thr Leu Gln Ala Phe Asp Ser His
    370                 375                 380 tat gac tac acc ata tgt ggg gac agt gaa gac atg gtg tgt acc ccc       1200
Tyr Asp Tyr Thr Ile Cys Gly Asp Ser Glu Asp Met Val Cys Thr Pro
385                 390                 395                 400 aag tcc gat gag ttc aac ccg tgt gaa gat cct cat cat cat cat cat       1248
Lys Ser Asp Glu Phe Asn Pro Cys Glu Asp Pro His His His His His
                405                 410                 415 cat taa                                                               1254
His
```

<210> SEQ ID NO 21
<211> LENGTH: 1254
<212> TYPE: DNA
<213> ORGANISM: Artificial/Unknown
<220> FEATURE:
<221> NAME/KEY: CDS
<222> LOCATION: (1)..(1254)
<223> OTHER INFORMATION: sTSHR

<400> SEQUENCE: 21

```
atg agg ccg gcg gac ttg ctg cag ctg gtg ctg ctc gac ctg ccc           48
Met Arg Pro Ala Asp Leu Leu Gln Leu Val Leu Leu Asp Leu Pro
1               5                  10                  15 agg gac ctg ggc gga atg ggg tgt tcg tct cca ccc tgc gag tgc cat       96
Arg Asp Leu Gly Gly Met Gly Cys Ser Ser Pro Pro Cys Glu Cys His
            20                  25                  30 cag gag gag gac ttc aga gtc acc tgc aag gat att caa cgc atc ccc      144
Gln Glu Glu Asp Phe Arg Val Thr Cys Lys Asp Ile Gln Arg Ile Pro
        35                  40                  45 agc tta ccg ccc agt acg cag act ctg aag ctt att gag act cac ctg      192
Ser Leu Pro Pro Ser Thr Gln Thr Leu Lys Leu Ile Glu Thr His Leu
```

-continued

```
                    50                          55                          60
aga act att cca agt cat gca ttt tct aat ctg ccc aat att tcc aga      240
Arg Thr Ile Pro Ser His Ala Phe Ser Asn Leu Pro Asn Ile Ser Arg
 65                  70                  75                  80 atc tac gta tct ata gat gtg act ctg cag cag ctg gaa tca cac tcc      288
Ile Tyr Val Ser Ile Asp Val Thr Leu Gln Gln Leu Glu Ser His Ser
                 85                  90                  95 ttc tac aat ttg agt aaa gtg act cac ata gaa att cgg aat acc agg      336
Phe Tyr Asn Leu Ser Lys Val Thr His Ile Glu Ile Arg Asn Thr Arg
             100                 105                 110 aac tta act tac ata gac cct gat gcc ctc aaa gag ctc ccc ctc cta      384
Asn Leu Thr Tyr Ile Asp Pro Asp Ala Leu Lys Glu Leu Pro Leu Leu
         115                 120                 125 aag ttc ctt ggc att ttc aac act gga ctt aaa atg ttc cct gac ctg      432
Lys Phe Leu Gly Ile Phe Asn Thr Gly Leu Lys Met Phe Pro Asp Leu
     130                 135                 140 acc aaa gtt tat tcc act gat ata ttc ttt ata ctt gaa att aca gac      480
Thr Lys Val Tyr Ser Thr Asp Ile Phe Phe Ile Leu Glu Ile Thr Asp
145                 150                 155                 160 aac cct tac atg acg tca atc cct gtg aat gct ttt cag gga cta tgc      528
Asn Pro Tyr Met Thr Ser Ile Pro Val Asn Ala Phe Gln Gly Leu Cys
                165                 170                 175 aat gaa acc ttg aca ctg aag ctg tac aac aac ggc ttt act tca gtc      576
Asn Glu Thr Leu Thr Leu Lys Leu Tyr Asn Asn Gly Phe Thr Ser Val
            180                 185                 190 caa gga tat gct ttc aat ggg aca aag ctg gat gct gtt tac cta aac      624
Gln Gly Tyr Ala Phe Asn Gly Thr Lys Leu Asp Ala Val Tyr Leu Asn
        195                 200                 205 aag aat aaa tac ctg aca gtt att gac aaa gat gca ttt gga gga gta      672
Lys Asn Lys Tyr Leu Thr Val Ile Asp Lys Asp Ala Phe Gly Gly Val
    210                 215                 220 tac agt gga cca agc ttg ctg gac gtg tct caa acc agt gtc act gcc      720
Tyr Ser Gly Pro Ser Leu Leu Asp Val Ser Gln Thr Ser Val Thr Ala
225                 230                 235                 240 ctt cca tcc aaa ggc ctg gag cac ctg aag gaa ctg ata gca aga aac      768
Leu Pro Ser Lys Gly Leu Glu His Leu Lys Glu Leu Ile Ala Arg Asn
                245                 250                 255 acc tgg act ctt aag aaa ctt cca ctt tcc ttg agt ttc ctt cac ctc      816
Thr Trp Thr Leu Lys Lys Leu Pro Leu Ser Leu Ser Phe Leu His Leu
            260                 265                 270 aca cgg gct gac ctt tct tac cca agc cac tgc tgt gcc ttt aag aat      864
Thr Arg Ala Asp Leu Ser Tyr Pro Ser His Cys Cys Ala Phe Lys Asn
        275                 280                 285 cag aag aaa atc aga gga atc ctt gag tcc ttg atg tgt aat gag agc      912
Gln Lys Lys Ile Arg Gly Ile Leu Glu Ser Leu Met Cys Asn Glu Ser
    290                 295                 300 agt atg cag agc ttg cgc cag aga aaa tct gtg aat gcc ttg aat agc      960
Ser Met Gln Ser Leu Arg Gln Arg Lys Ser Val Asn Ala Leu Asn Ser
305                 310                 315                 320 ccc ctc cac cag gaa tat gaa gag aat ctg ggt gac agc att gtt ggg     1008
Pro Leu His Gln Glu Tyr Glu Glu Asn Leu Gly Asp Ser Ile Val Gly
                325                 330                 335 tac aag gaa aag tcc aag ttc cag gat act cat aac aac gct cat gct     1056
Tyr Lys Glu Lys Ser Lys Phe Gln Asp Thr His Asn Asn Ala His Ala
            340                 345                 350 gcg gcc gca gct gaa gaa caa gag gat gag atc att ggt ttt ggc cag     1104
Ala Ala Ala Ala Glu Glu Gln Glu Asp Glu Ile Ile Gly Phe Gly Gln
        355                 360                 365 gag ctc aaa aac ccc cag gaa gag act cta caa gct ttt gac agc cat     1152
Glu Leu Lys Asn Pro Gln Glu Glu Thr Leu Gln Ala Phe Asp Ser His
```

-continued

| | | | | | | | | | | | | |
|---|---|---|---|---|---|---|---|---|---|---|---|---|
| Glu | Leu | Lys | Asn | Pro | Gln | Glu | Thr | Leu | Gln | Ala | Phe | Asp | Ser | His |
| | 370 | | | | 375 | | | | 380 | | | | | tat gac tac acc ata tgt ggg gac agt gaa gac atg gtg tgt acc ccc   1200
Tyr Asp Tyr Thr Ile Cys Gly Asp Ser Glu Asp Met Val Cys Thr Pro
385                 390                 395                 400 aag tcc gat gag ttc aac ccg tgt gaa gat cct cat cat cat cat cat   1248
Lys Ser Asp Glu Phe Asn Pro Cys Glu Asp Pro His His His His His
              405                 410                 415 cat taa                                                            1254
His

<210> SEQ ID NO 22
<211> LENGTH: 1167
<212> TYPE: DNA
<213> ORGANISM: Artificial/Unknown
<220> FEATURE:
<221> NAME/KEY: CDS
<222> LOCATION: (1)..(1167)
<223> OTHER INFORMATION: sTSHR

<400> SEQUENCE: 22 atg agg ccg gcg gac ttg ctg cag ctg gtg ctg ctg ctc gac ctg ccc   48
Met Arg Pro Ala Asp Leu Leu Gln Leu Val Leu Leu Leu Asp Leu Pro
1               5                   10                  15 agg gac ctg ggc gga atg ggg tgt tcg tct cca ccc tgc gag tgc cat   96
Arg Asp Leu Gly Gly Met Gly Cys Ser Ser Pro Pro Cys Glu Cys His
              20                  25                  30 cag gag gag gac ttc aga gtc acc tgc aag gat att caa cgc atc ccc   144
Gln Glu Glu Asp Phe Arg Val Thr Cys Lys Asp Ile Gln Arg Ile Pro
          35                  40                  45 agc tta ccg ccc agt acg cag act ctg aag ctt att gag act cac ctg   192
Ser Leu Pro Pro Ser Thr Gln Thr Leu Lys Leu Ile Glu Thr His Leu
50                  55                  60 aga act att cca agt cat gca ttt tct aat ctg ccc aat att tcc aga   240
Arg Thr Ile Pro Ser His Ala Phe Ser Asn Leu Pro Asn Ile Ser Arg
65                  70                  75                  80 atc tac gta tct ata gat gtg act ctg cag cag ctg gaa tca cac tcc   288
Ile Tyr Val Ser Ile Asp Val Thr Leu Gln Gln Leu Glu Ser His Ser
                85                  90                  95 ttc tac aat ttg agt aaa gtg act cac ata gaa att cgg aat acc agg   336
Phe Tyr Asn Leu Ser Lys Val Thr His Ile Glu Ile Arg Asn Thr Arg
            100                 105                 110 aac tta act tac ata gac cct gat gcc ctc aaa gag ctc ccc ctc cta   384
Asn Leu Thr Tyr Ile Asp Pro Asp Ala Leu Lys Glu Leu Pro Leu Leu
        115                 120                 125 aag ttc ctt ggc att ttc aac act gga ctt aaa atg ttc cct gac ctg   432
Lys Phe Leu Gly Ile Phe Asn Thr Gly Leu Lys Met Phe Pro Asp Leu
    130                 135                 140 acc aaa gtt tat tcc act gat ata ttc ttt ata ctt gaa att aca gac   480
Thr Lys Val Tyr Ser Thr Asp Ile Phe Phe Ile Leu Glu Ile Thr Asp
145                 150                 155                 160 aac cct tac atg acg tca atc cct gtg aat gct ttt cag gga cta tgc   528
Asn Pro Tyr Met Thr Ser Ile Pro Val Asn Ala Phe Gln Gly Leu Cys
                165                 170                 175 aat gaa acc ttg aca ctg aag ctg tac aac aac ggc ttt act tca gtc   576
Asn Glu Thr Leu Thr Leu Lys Leu Tyr Asn Asn Gly Phe Thr Ser Val
            180                 185                 190 caa gga tat gct ttc aat ggg aca aag ctg gat gct gtt tac cta aac   624
Gln Gly Tyr Ala Phe Asn Gly Thr Lys Leu Asp Ala Val Tyr Leu Asn
        195                 200                 205 aag aat aaa tac ctg aca gtt att gac aaa gat gca ttt gga gga gta   672

-continued

```
                Lys Asn Lys Tyr Leu Thr Val Ile Asp Lys Asp Ala Phe Gly Gly Val
                    210                 215                 220 tac agt gga cca agc ttg ctg gac gtg tct caa acc agt gtc act gcc        720
Tyr Ser Gly Pro Ser Leu Leu Asp Val Ser Gln Thr Ser Val Thr Ala
225                 230                 235                 240 ctt cca tcc aaa ggc ctg gag cac ctg aag gaa ctg ata gca aga aac        768
Leu Pro Ser Lys Gly Leu Glu His Leu Lys Glu Leu Ile Ala Arg Asn
                245                 250                 255 acc tgg act ctt aag aaa ctt cca ctt tcc ttg agt ttc ctt cac ctc        816
Thr Trp Thr Leu Lys Lys Leu Pro Leu Ser Leu Ser Phe Leu His Leu
                260                 265                 270 aca cgg gct gac ctt tct tac cca agc cac tgc tgt gcc ttt aag aat        864
Thr Arg Ala Asp Leu Ser Tyr Pro Ser His Cys Cys Ala Phe Lys Asn
                275                 280                 285 cag aag aaa atc aga gga atc ctt gag tcc ttg atg tgt aat gag agc        912
Gln Lys Lys Ile Arg Gly Ile Leu Glu Ser Leu Met Cys Asn Glu Ser
            290                 295                 300 agt atg cag agc ttg cgc cag aga aaa tct gtg aat gcc ttg aat agc        960
Ser Met Gln Ser Leu Arg Gln Arg Lys Ser Val Asn Ala Leu Asn Ser
305                 310                 315                 320 ccc ctc cac cag gaa tat gaa gag aat ctg ggt gac agc att gtt ggg       1008
Pro Leu His Gln Glu Tyr Glu Glu Asn Leu Gly Asp Ser Ile Val Gly
                325                 330                 335 tac ggc cag gag ctc aaa aac ccc cag gaa gag act cta caa gct ttt       1056
Tyr Gly Gln Glu Leu Lys Asn Pro Gln Glu Glu Thr Leu Gln Ala Phe
                340                 345                 350 gac agc cat tat gac tac acc ata tgt ggg gac agt gaa gac atg gtg       1104
Asp Ser His Tyr Asp Tyr Thr Ile Cys Gly Asp Ser Glu Asp Met Val
                355                 360                 365 tgt acc ccc aag tcc gat gag ttc aac ccg tgt gaa gat cct cat cat       1152
Cys Thr Pro Lys Ser Asp Glu Phe Asn Pro Cys Glu Asp Pro His His
        370                 375                 380 cat cat cat cat taa                                                    1167
His His His His
385

<210> SEQ ID NO 23
<211> LENGTH: 1269
<212> TYPE: DNA
<213> ORGANISM: Artificial/Unknown
<220> FEATURE:
<221> NAME/KEY: CDS
<222> LOCATION: (1)..(1269)
<223> OTHER INFORMATION: sTSHR

<400> SEQUENCE: 23 atg agg ccg gcg gac ttg ctg cag ctg gtg ctg ctc gac ctg ccc            48
Met Arg Pro Ala Asp Leu Leu Gln Leu Val Leu Leu Asp Leu Pro
1               5                   10                  15 agg gac ctg ggc gga atg ggg tgt tcg tct cca ccc tgc gag tgc cat        96
Arg Asp Leu Gly Gly Met Gly Cys Ser Ser Pro Pro Cys Glu Cys His
                20                  25                  30 cag gag gag gac ttc aga gtc acc tgc aag gat att caa cgc atc ccc       144
Gln Glu Glu Asp Phe Arg Val Thr Cys Lys Asp Ile Gln Arg Ile Pro
            35                  40                  45 agc tta ccg ccc agt acg cag act ctg aag ctt att gag act cac ctg       192
Ser Leu Pro Pro Ser Thr Gln Thr Leu Lys Leu Ile Glu Thr His Leu
        50                  55                  60 aga act att cca agt cat gca ttt tct aat ctg ccc aat att tcc aga       240
Arg Thr Ile Pro Ser His Ala Phe Ser Asn Leu Pro Asn Ile Ser Arg
65                  70                  75                  80
```

```
atc tac gta tct ata gat gtg act ctg cag cag ctg gaa tca cac tcc    288
Ile Tyr Val Ser Ile Asp Val Thr Leu Gln Gln Leu Glu Ser His Ser
             85                  90                  95 ttc tac aat ttg agt aaa gtg act cac ata gaa att cgg aat acc agg    336
Phe Tyr Asn Leu Ser Lys Val Thr His Ile Glu Ile Arg Asn Thr Arg
            100                 105                 110 aac tta act tac ata gac cct gat gcc ctc aaa gag ctc ccc ctc cta    384
Asn Leu Thr Tyr Ile Asp Pro Asp Ala Leu Lys Glu Leu Pro Leu Leu
            115                 120                 125 aag ttc ctt ggc att ttc aac act gga ctt aaa atg ttc cct gac ctg    432
Lys Phe Leu Gly Ile Phe Asn Thr Gly Leu Lys Met Phe Pro Asp Leu
        130                 135                 140 acc aaa gtt tat tcc act gat ata ttc ttt ata ctt gaa att aca gac    480
Thr Lys Val Tyr Ser Thr Asp Ile Phe Phe Ile Leu Glu Ile Thr Asp
145                 150                 155                 160 aac cct tac atg acg tca atc cct gtg aat gct ttt cag gga cta tgc    528
Asn Pro Tyr Met Thr Ser Ile Pro Val Asn Ala Phe Gln Gly Leu Cys
                165                 170                 175 aat gaa acc ttg aca ctg aag ctg tac aac aac ggc ttt act tca gtc    576
Asn Glu Thr Leu Thr Leu Lys Leu Tyr Asn Asn Gly Phe Thr Ser Val
            180                 185                 190 caa gga tat gct ttc aat ggg aca aag ctg gat gct gtt tac cta aac    624
Gln Gly Tyr Ala Phe Asn Gly Thr Lys Leu Asp Ala Val Tyr Leu Asn
        195                 200                 205 aag aat aaa tac ctg aca gtt att gac aaa gat gca ttt gga gga gta    672
Lys Asn Lys Tyr Leu Thr Val Ile Asp Lys Asp Ala Phe Gly Gly Val
    210                 215                 220 tac agt gga cca agc ttg ctg gac gtg tct caa acc agt gtc act gcc    720
Tyr Ser Gly Pro Ser Leu Leu Asp Val Ser Gln Thr Ser Val Thr Ala
225                 230                 235                 240 ctt cca tcc aaa ggc ctg gag cac ctg aag gaa ctg ata gca aga aac    768
Leu Pro Ser Lys Gly Leu Glu His Leu Lys Glu Leu Ile Ala Arg Asn
                245                 250                 255 acc tgg act ctt aag aaa ctt cca ctt tcc ttg agt ttc ctt cac ctc    816
Thr Trp Thr Leu Lys Lys Leu Pro Leu Ser Leu Ser Phe Leu His Leu
            260                 265                 270 aca cgg gct gac ctt tct tac cca agc cac tgc tgt gcc ttt aag aat    864
Thr Arg Ala Asp Leu Ser Tyr Pro Ser His Cys Cys Ala Phe Lys Asn
        275                 280                 285 cag aag aaa atc aga gga atc ctt gag tcc ttg atg tgt aat gag agc    912
Gln Lys Lys Ile Arg Gly Ile Leu Glu Ser Leu Met Cys Asn Glu Ser
    290                 295                 300 agt atg cag agc ttg cgc cag aga aaa tct gtg aat gcc ttg aat agc    960
Ser Met Gln Ser Leu Arg Gln Arg Lys Ser Val Asn Ala Leu Asn Ser
305                 310                 315                 320 ccc ctc cac cag gaa tat gaa gag aat ctg ggt gac agc att gtt ggg   1008
Pro Leu His Gln Glu Tyr Glu Glu Asn Leu Gly Asp Ser Ile Val Gly
                325                 330                 335 tac aag gaa aag tcc aag ttc cag gat act cat aac aac gct cat tat   1056
Tyr Lys Glu Lys Ser Lys Phe Gln Asp Thr His Asn Asn Ala His Tyr
            340                 345                 350 tac gtc ttc ttt gaa gaa caa gag gat gag atc att ggt ttt ggc cag   1104
Tyr Val Phe Phe Glu Glu Gln Glu Asp Glu Ile Ile Gly Phe Gly Gln
        355                 360                 365 gag ctc aaa aac ccc cag gaa gag act cta caa gct ttt gac agc cat   1152
Glu Leu Lys Asn Pro Gln Glu Glu Thr Leu Gln Ala Phe Asp Ser His
    370                 375                 380 tat gac tac acc ata tgt ggg gac agt gaa gac atg gtg tgt acc ccc   1200
Tyr Asp Tyr Thr Ile Cys Gly Asp Ser Glu Asp Met Val Cys Thr Pro
385                 390                 395                 400
```

```
aag tcc gat gag ttc aac ccg tgt gaa gac ata atg ggc tac aag cct    1248
Lys Ser Asp Glu Phe Asn Pro Cys Glu Asp Ile Met Gly Tyr Lys Pro
            405                 410                 415 cat cat cat cat cat cat taa                                        1269
His His His His His His
            420

<210> SEQ ID NO 24
<211> LENGTH: 1320
<212> TYPE: DNA
<213> ORGANISM: Artificial/Unknown
<220> FEATURE:
<221> NAME/KEY: CDS
<222> LOCATION: (1)..(1320)
<223> OTHER INFORMATION: sTSHR

<400> SEQUENCE: 24 atg cta cta gta aat cag tca cac caa ggc ttc aat aag gaa cac aca      48
Met Leu Leu Val Asn Gln Ser His Gln Gly Phe Asn Lys Glu His Thr
1               5                   10                  15 agc aag atg gta agc gct att gtt tta tat gtg ctt ttg gcg gcg gcg     96
Ser Lys Met Val Ser Ala Ile Val Leu Tyr Val Leu Leu Ala Ala Ala
            20                  25                  30 gcg cat tct gcc ttt gcg gcg gat gaa ttc gga atg ggg tgt tcg tct    144
Ala His Ser Ala Phe Ala Ala Asp Glu Phe Gly Met Gly Cys Ser Ser
        35                  40                  45 cca ccc tgc gag tgc cat cag gag gag gac ttc aga gtc acc tgc aag    192
Pro Pro Cys Glu Cys His Gln Glu Glu Asp Phe Arg Val Thr Cys Lys
    50                  55                  60 gat att caa cgc atc ccc agc tta ccg ccc agt acg cag act ctg aag    240
Asp Ile Gln Arg Ile Pro Ser Leu Pro Pro Ser Thr Gln Thr Leu Lys
65                  70                  75                  80 ctt att gag act cac ctg aga act att cca agt cat gca ttt tct aat    288
Leu Ile Glu Thr His Leu Arg Thr Ile Pro Ser His Ala Phe Ser Asn
                85                  90                  95 ctg ccc aat att tcc aga atc tac gta tct ata gat gtg act ctg cag    336
Leu Pro Asn Ile Ser Arg Ile Tyr Val Ser Ile Asp Val Thr Leu Gln
            100                 105                 110 cag ctg gaa tca cac tcc ttc tac aat ttg agt aaa gtg act cac ata    384
Gln Leu Glu Ser His Ser Phe Tyr Asn Leu Ser Lys Val Thr His Ile
        115                 120                 125 gaa att cgg aat acc agg aac tta act tac ata gac cct gat gcc ctc    432
Glu Ile Arg Asn Thr Arg Asn Leu Thr Tyr Ile Asp Pro Asp Ala Leu
    130                 135                 140 aaa gag ctc ccc ctc cta aag ttc ctt ggc att ttc aac act gga ctt    480
Lys Glu Leu Pro Leu Leu Lys Phe Leu Gly Ile Phe Asn Thr Gly Leu
145                 150                 155                 160 aaa atg ttc cct gac ctg acc aaa gtt tat tcc act gat ata ttc ttt    528
Lys Met Phe Pro Asp Leu Thr Lys Val Tyr Ser Thr Asp Ile Phe Phe
                165                 170                 175 ata ctt gaa att aca gac aac cct tac atg acg tca atc cct gtg aat    576
Ile Leu Glu Ile Thr Asp Asn Pro Tyr Met Thr Ser Ile Pro Val Asn
            180                 185                 190 gct ttt cag gga cta tgc aat gaa acc ttg aca ctg aag ctg tac aac    624
Ala Phe Gln Gly Leu Cys Asn Glu Thr Leu Thr Leu Lys Leu Tyr Asn
        195                 200                 205 aac ggc ttt act tca gtc caa gga tat gct ttc aat ggg aca aag ctg    672
Asn Gly Phe Thr Ser Val Gln Gly Tyr Ala Phe Asn Gly Thr Lys Leu
    210                 215                 220 gat gct gtt tac cta aac aag aat aaa tac ctg aca gtt att gac aaa    720
Asp Ala Val Tyr Leu Asn Lys Asn Lys Tyr Leu Thr Val Ile Asp Lys
```

```
gat gca ttt gga gga gta tac agt gga cca agc ttg ctg gac gtg tct     768
Asp Ala Phe Gly Gly Val Tyr Ser Gly Pro Ser Leu Leu Asp Val Ser
            245                 250                 255 caa acc agt gtc act gcc ctt cca tcc aaa ggc ctg gag cac ctg aag     816
Gln Thr Ser Val Thr Ala Leu Pro Ser Lys Gly Leu Glu His Leu Lys
            260                 265                 270 gaa ctg ata gca aga aac acc tgg act ctt aag aaa ctt cca ctt tcc     864
Glu Leu Ile Ala Arg Asn Thr Trp Thr Leu Lys Lys Leu Pro Leu Ser
        275                 280                 285 ttg agt ttc ctt cac ctc aca cgg gct gac ctt tct tac cca agc cac     912
Leu Ser Phe Leu His Leu Thr Arg Ala Asp Leu Ser Tyr Pro Ser His
        290                 295                 300 tgc tgt gcc ttt aag aat cag aag aaa atc aga gga atc ctt gag tcc     960
Cys Cys Ala Phe Lys Asn Gln Lys Lys Ile Arg Gly Ile Leu Glu Ser
305                 310                 315                 320 ttg atg tgt aat gag agc agt atg cag agc ttg cgc cag aga aaa tct    1008
Leu Met Cys Asn Glu Ser Ser Met Gln Ser Leu Arg Gln Arg Lys Ser
                325                 330                 335 gtg aat gcc ttg aat agc ccc ctc cac cag gaa tat gaa gag aat ctg    1056
Val Asn Ala Leu Asn Ser Pro Leu His Gln Glu Tyr Glu Glu Asn Leu
            340                 345                 350 ggt gac agc att gtt ggg tac aag gaa aag tcc aag ttc cag gat act    1104
Gly Asp Ser Ile Val Gly Tyr Lys Glu Lys Ser Lys Phe Gln Asp Thr
        355                 360                 365 cat aac aac gct cat tat tac gtc ttt ttt gaa gaa caa gag gat gag    1152
His Asn Asn Ala His Tyr Tyr Val Phe Phe Glu Glu Gln Glu Asp Glu
        370                 375                 380 atc att ggt ttt ggc cag gag ctc aaa aac ccc cag gaa gag act cta    1200
Ile Ile Gly Phe Gly Gln Glu Leu Lys Asn Pro Gln Glu Glu Thr Leu
385                 390                 395                 400 caa gct ttt gac agc cat tat gac tac acc ata tgt ggg gac agt gaa    1248
Gln Ala Phe Asp Ser His Tyr Asp Tyr Thr Ile Cys Gly Asp Ser Glu
                405                 410                 415 gac atg gtg tgt acc ccc aag tcc gat gag ttc aac ccg tgt gaa gac    1296
Asp Met Val Cys Thr Pro Lys Ser Asp Glu Phe Asn Pro Cys Glu Asp
            420                 425                 430 cct cat cat cat cat cat cat taa                                    1320
Pro His His His His His His
        435
```

<210> SEQ ID NO 25
<211> LENGTH: 1335
<212> TYPE: DNA
<213> ORGANISM: Artificial/Unknown
<220> FEATURE:
<221> NAME/KEY: CDS
<222> LOCATION: (1)..(1335)
<223> OTHER INFORMATION: sTSHR

<400> SEQUENCE: 25

```
atg cta cta gta aat cag tca cac caa ggc ttc aat aag gaa cac aca      48
Met Leu Leu Val Asn Gln Ser His Gln Gly Phe Asn Lys Glu His Thr
1               5                   10                  15 agc aag atg gta agc gct att gtt tta tat gtg ctt ttg gcg gcg gcg      96
Ser Lys Met Val Ser Ala Ile Val Leu Tyr Val Leu Leu Ala Ala Ala
                20                  25                  30 gcg cat tct gcc ttt gcg gcg gat gaa ttc gga atg ggg tgt tcg tct     144
Ala His Ser Ala Phe Ala Ala Asp Glu Phe Gly Met Gly Cys Ser Ser
            35                  40                  45 cca ccc tgc gag tgc cat cag gag gag gac ttc aga gtc acc tgc aag     192
```

```
Pro Pro Cys Glu Cys His Gln Glu Glu Asp Phe Arg Val Thr Cys Lys
    50                  55                  60 gat att caa cgc atc ccc agc tta ccg ccc agt acg cag act ctg aag      240
Asp Ile Gln Arg Ile Pro Ser Leu Pro Pro Ser Thr Gln Thr Leu Lys
 65                  70                  75                  80 ctt att gag act cac ctg aga act att cca agt cat gca ttt tct aat      288
Leu Ile Glu Thr His Leu Arg Thr Ile Pro Ser His Ala Phe Ser Asn
                 85                  90                  95 ctg ccc aat att tcc aga atc tac gta tct ata gat gtg act ctg cag      336
Leu Pro Asn Ile Ser Arg Ile Tyr Val Ser Ile Asp Val Thr Leu Gln
                100                 105                 110 cag ctg gaa tca cac tcc ttc tac aat ttg agt aaa gtg act cac ata      384
Gln Leu Glu Ser His Ser Phe Tyr Asn Leu Ser Lys Val Thr His Ile
            115                 120                 125 gaa att cgg aat acc agg aac tta act tac ata gac cct gat gcc ctc      432
Glu Ile Arg Asn Thr Arg Asn Leu Thr Tyr Ile Asp Pro Asp Ala Leu
        130                 135                 140 aaa gag ctc ccc ctc cta aag ttc ctt ggc att ttc aac act gga ctt      480
Lys Glu Leu Pro Leu Leu Lys Phe Leu Gly Ile Phe Asn Thr Gly Leu
145                 150                 155                 160 aaa atg ttc cct gac ctg acc aaa gtt tat tcc act gat ata ttc ttt      528
Lys Met Phe Pro Asp Leu Thr Lys Val Tyr Ser Thr Asp Ile Phe Phe
                165                 170                 175 ata ctt gaa att aca gac aac cct tac atg acg tca atc cct gtg aat      576
Ile Leu Glu Ile Thr Asp Asn Pro Tyr Met Thr Ser Ile Pro Val Asn
                180                 185                 190 gct ttt cag gga cta tgc aat gaa acc ttg aca ctg aag ctg tac aac      624
Ala Phe Gln Gly Leu Cys Asn Glu Thr Leu Thr Leu Lys Leu Tyr Asn
            195                 200                 205 aac ggc ttt act tca gtc caa gga tat gct ttc aat ggg aca aag ctg      672
Asn Gly Phe Thr Ser Val Gln Gly Tyr Ala Phe Asn Gly Thr Lys Leu
        210                 215                 220 gat gct gtt tac cta aac aag aat aaa tac ctg aca gtt att gac aaa      720
Asp Ala Val Tyr Leu Asn Lys Asn Lys Tyr Leu Thr Val Ile Asp Lys
225                 230                 235                 240 gat gca ttt gga gga gta tac agt gga cca agc ttg ctg gac gtg tct      768
Asp Ala Phe Gly Gly Val Tyr Ser Gly Pro Ser Leu Leu Asp Val Ser
                245                 250                 255 caa acc agt gtc act gcc ctt cca tcc aaa ggc ctg gag cac ctg aag      816
Gln Thr Ser Val Thr Ala Leu Pro Ser Lys Gly Leu Glu His Leu Lys
            260                 265                 270 gaa ctg ata gca aga aac acc tgg act ctt aag aaa ctt cca ctt tcc      864
Glu Leu Ile Ala Arg Asn Thr Trp Thr Leu Lys Lys Leu Pro Leu Ser
        275                 280                 285 ttg agt ttc ctt cac ctc aca cgg gct gac ctt tct tac cca agc cac      912
Leu Ser Phe Leu His Leu Thr Arg Ala Asp Leu Ser Tyr Pro Ser His
    290                 295                 300 tgc tgt gcc ttt aag aat cag aag aaa atc aga gga atc ctt gag tcc      960
Cys Cys Ala Phe Lys Asn Gln Lys Lys Ile Arg Gly Ile Leu Glu Ser
305                 310                 315                 320 ttg atg tgt aat gag agc agt atg cag agc ttg cgc cag aga aaa tct     1008
Leu Met Cys Asn Glu Ser Ser Met Gln Ser Leu Arg Gln Arg Lys Ser
                325                 330                 335 gtg aat gcc ttg aat agc ccc ctc cac cag gaa tat gaa gag aat ctg     1056
Val Asn Ala Leu Asn Ser Pro Leu His Gln Glu Tyr Glu Glu Asn Leu
            340                 345                 350 ggt gac agc att gtt ggg tac aag gaa aag tcc aag ttc cag gat act     1104
Gly Asp Ser Ile Val Gly Tyr Lys Glu Lys Ser Lys Phe Gln Asp Thr
        355                 360                 365
```

-continued

| | | | | | | | | | | | | | | | |
|---|---|---|---|---|---|---|---|---|---|---|---|---|---|---|---|
| cat | aac | aac | gct | cat | tat | tac | gtc | ttc | ttt | gaa | gaa | caa | gag | gat | gag | 1152 |
| His | Asn | Asn | Ala | His | Tyr | Tyr | Val | Phe | Phe | Glu | Glu | Gln | Glu | Asp | Glu |
| | 370 | | | | 375 | | | | | 380 | | | | | |
| atc | att | ggt | ttt | ggc | cag | gag | ctc | aaa | aac | ccc | cag | gaa | gag | act | cta | 1200 |
| Ile | Ile | Gly | Phe | Gly | Gln | Glu | Leu | Lys | Asn | Pro | Gln | Glu | Glu | Thr | Leu |
| 385 | | | | | 390 | | | | | 395 | | | | | 400 |
| caa | gct | ttt | gac | agc | cat | tat | gac | tac | acc | ata | tgt | ggg | gac | agt | gaa | 1248 |
| Gln | Ala | Phe | Asp | Ser | His | Tyr | Asp | Tyr | Thr | Ile | Cys | Gly | Asp | Ser | Glu |
| | | | | 405 | | | | | 410 | | | | | 415 | |
| gac | atg | gtg | tgt | acc | ccc | aag | tcc | gat | gag | ttc | aac | ccg | tgt | gaa | gac | 1296 |
| Asp | Met | Val | Cys | Thr | Pro | Lys | Ser | Asp | Glu | Phe | Asn | Pro | Cys | Glu | Asp |
| | | | 420 | | | | | 425 | | | | | 430 | | |
| ata | atg | ggc | tac | aag | cct | cat | cat | cat | cat | cat | cat | taa | | | | 1335 |
| Ile | Met | Gly | Tyr | Lys | Pro | His | His | His | His | His | His |
| | | 435 | | | | | | 440 | | | | |

SECRETORY THYROID STIMULATING HORMONE RECEPTOR, AND METHOD FOR ASSAYING ANTI-THYROID STIMULATING HORMONE RECEPTOR ANTIBODY USING THE SAME

BACKGROUND OF THE INVENTION

1. Field of the Invention

The present invention relates to a recombinant soluble human thyroid hormone receptor (hereinafter referred to as "sTSHR") which is secretory and has reactivity with an anti-human thyroid stimulating hormone receptor autoantibody; a process for producing sTSHR, comprising infecting an insect cell, particularly Hi five cell, with a recombinant *baculovirus* prepared by inserting a gene encoding sTSHR, and culturing the infected cells; a reagent for assaying an anti-human thyroid stimulating hormone receptor antibody, such as an autoantibody, using sTSHR; and a method for measuring an anti-human thyroid stimulating hormone receptor antibody, such as an autoantibody, using sTSHR.

2. Brief Description of the Background Art

A human thyroid stimulating hormone receptor (hereinafter referred to as "TSHR") is a receptor of thyroid stimulating hormone (hereinafter referred to as "TSH") which is present on the thyroid membrane. When TSH secreted from the pituitary gland binds to TSHR on the thyroid follicle cell membrane, the thyroid gland secretes T3 and T4 having metabolic functions. TSHR is a seven transmembrane receptor having a molecular weight of about 95,000 to 100,000.

Graves' disease is a hyperthyroidism induced by the acceleration of formation and secretion of thyroid hormones. As its cause, the presence of a stimulative substance which quickens secretion of thyroid hormones in patient's serum can be enumerated. It is known from the studies until now that an autoantibody for TSHR is present in patient's serum and induces hyperthyroidism by activating a thyroid stimulating hormone receptor. Thus, the measurement of the autoantibody for TSHR has a considerable significance in carrying out clinical diagnosis.

The measurement of an anti-TSHR autoantibody has so far been carried out by the method developed by Smith (*Endocr. Rev.*, 9: 106–120 (1988)). In this method, the anti-TSHR autoantibody is measured by using a porcine thyroid gland membrane fraction as the TSHR source and by allowing $^{125}$I-labeled bovine TSH and an anti-TSHR autoantibody in patient's serum to compete with each other for the TSHR source.

However, since a cross reaction, namely binding of porcine TSHR to an anti-human TSHR autoantibody in human serum, is examined in the conventional method, there is a possibility that the assay result does not correctly reflect binding of human TSHR originally formed in the living body to the anti-human TSHR autoantibody in human serum. Also, since sequences of amino acid residues of human TSHR and porcine TSHR are actually different from each other, it is expected that the results of the conventional method do not coincide with the binding of the human TSHR autoantibody to the human TSHR. In addition to these problems, there is another problem in that it is difficult to prepare the porcine thyroid gland membrane fraction used as the TSHR source at a large amount.

Naturally, it is preferred to use human TSHR for the measurement of an autoantibody for human TSHR. However, since it is impossible in reality to obtain natural TSHR from human, attempts have been made to prepare it by genetic recombination techniques. Particularly, in order to purify TSHR by expressing it at a large amount, it is important to create TSHR which has reactivity with anti-human TSHR antibody and is secretory.

TSHR is a seven transmembrane receptor and its first N-terminus extracellular domain occupies the majority of TSHR, so that it is considered that the binding region for an anti-human TSHR autoantibody is present in this region. Although attempts have so far been made by a plurality of research groups to express soluble TSHR constituted by the first N-terminus extracellular domain of TSHR at a large amount using insect cells or animal cells, the expressed soluble TSHR is accumulated as an insoluble protein inside the cells in each case, without success in effecting extracellular secretion and purifying a large amount of the soluble TSHR (*Journal of Molecular Endocrinology*, 10: 127–142 (1993)); *Endocrinology*, 138: 1658–1666 (1997); *The Journal of Biological Chemistry*, 270: 1543–1549 (1995); *Journal of Immunology*, 158; 2798–2804 (1997); *Molecular and Cellular Endocrinology*, 147: 133–142 (1999); *Endocrinology*, 138: 1559–1566 (1997); *Autoimmunity*, 14: 315–320 (1993)). In addition, it has been reported that the soluble TSHR does not have affinity for TSH and shows only a weak reactivity for an anti-TSHR antibody existing in serum from patients with Graves' disease.

It has been reported that a soluble TSHR (aal-309) in which 106 amino acid residues were deleted from the extracellular domain C-terminus of TSHR was secreted into extracellular moiety in CHO cells (*The Journal of Biological Chemistry*, 272: 18959–18965 (1997)). However, this C-terminus deleted soluble TSHR does not have affinity for TSH, and it is considered that epitope of an anti-TSHR antibody derived from patients with Graves' disease is also present in the deleted region, so that it cannot be used in the measurement of anti-TSHR autoantibodies.

SUMMARY OF THE INVENTION

Objects of the present invention are to provide a recombinant soluble human thyroid hormone receptor (sTSHR) which is secretory and has reactivity with an anti-human thyroid stimulating hormone receptor autoantibody; a process for producing sTSHR, a reagent using sTSHR, and a measuring method which uses sTSHR.

These objects and others are provided by the present invention, which relates to the following (1) to (12).

(1) A recombinant soluble human thyroid hormone receptor, comprising an extracellular domain moiety of a human thyroid hormone receptor, or a mutant thereof,
   being secretory, and
   having reactivity with an anti-human thyroid stimulating hormone receptor autoantibody.

(2) The receptor according to (1), which comprises 395 amino acid residues of the 21st to the 415th from the N-terminus of a native human thyroid hormone receptor.

(3) The receptor according to (1), which comprises 390 amino acid residues of the 21st to the 410th from the N-terminus of a native human thyroid hormone receptor.

(4) The receptor according to any one of (1) to (3), which comprises amino acid residues of the 338th to the 366th from the N-terminus of a native human thyroid hormone receptor which is subjected to at least one mutation selected from deletion, substitution, insertion and addition.

(5) The receptor according to any one of (1) to (3), which comprises amino acid residues of the 352nd to the 356th from the N-terminus of a native human thyroid hormone receptor which is subjected to at least one mutation selected from deletion, substitution, insertion and addition.
(6) The receptor according to any one of (1) to (5), which has affinity for a thyroid stimulating hormone.
(7) The receptor according to any one of (1) to (6), which is capable of expressing in an insect Hi five cell.
(8) A composition for assaying an anti-human thyroid stimulating hormone receptor antibody, comprising the receptor of any one of (1) to (7), and a carrier or diluent.
(9) A method for assaying an anti-human thyroid stimulating hormone receptor antibody, comprising reacting an anti-human thyroid stimulating hormone receptor antibody with the receptor of any one of (1) to (7).
(10) A method for producing a recombinant soluble human thyroid hormone receptor which is secretory and has reactivity with an anti-human thyroid stimulating hormone receptor autoantibody, comprising infecting an insect cell with a recombinant *baculovirus* introduced with an extracellular domain moiety of a gene encoding a human thyroid hormone receptor or a mutant thereof, and culturing the infected cell.
(11) The method according to (10), wherein the gene has a nucleotide sequence encoding a *baculovirus* signal sequence on its 5' end.
(12) The process according to (10), wherein the insect cell is an insect Hi five cell.

BRIEF EXPLANATION OF THE DRAWINGS

FIG. 4 shows a result of the detection of sTSHR protein purified from a culture supernatant fraction (B) and a cell extract fraction (A) using a ConA column or lentil lectin column, carried out by Western blotting using an anti-His$_6$ antibody.

FIG. 8 shows a result of experimentation on whether or not TSAb activity can be absorbed by allowing sera from patients with Graves' disease having TSAb activity to react with sTSHR in advance.

FIG. 10 shows a result of the reaction of sera from patients with Graves' disease or hypothyroidism patients, or sera from health persons in a case (+) in which sTSHR purified by metal affinity chromatography from a culture supernatant fraction was immobilized on a nickel-immobilized 96 well plate by chelate binding or another case (−) in which a crude purification fraction of sTSHR was not immobilized.

DETAILED DESCRIPTION OF THE INVENTION 1. sTSHR

Figure 1:
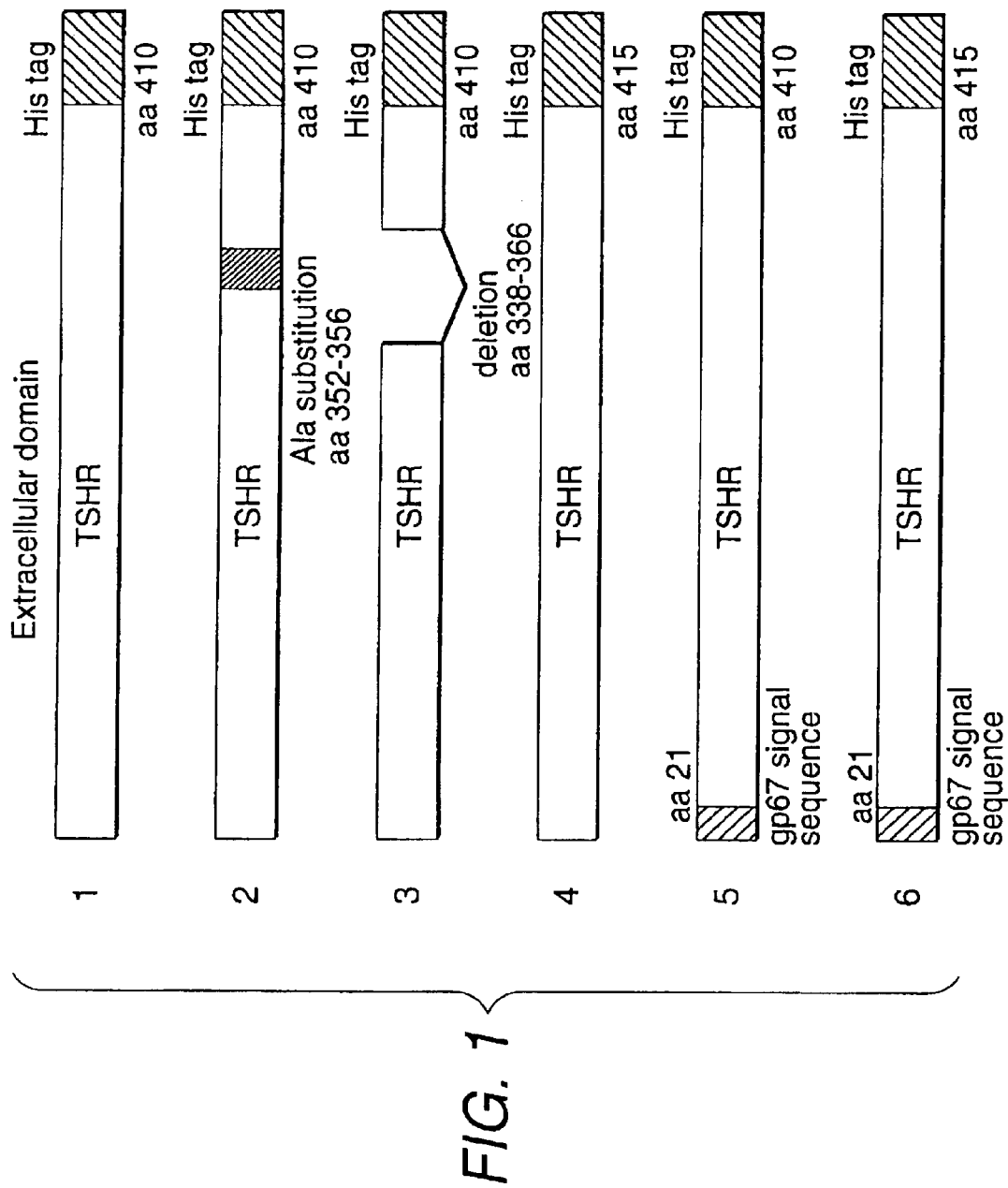
FIG. 1 schematically shows structures of the sTSHR (6 kinds) of the present invention expressed in Examples. The sTSHR include those in which 6 histidine residues are added to C terminal of amino acid residues (the 1st to the 410th from the N-terminus) of an extracellular domain moiety of the natural TSHR (SEQ ID NOs: 5 and 20), in which a moiety of amino acid residues of 338th to the 366th from the N-terminus of TSHR is deleted (SEQ ID NOs: 11 and 22), in which each amino acid residue in an amino acid residue moiety of the 352nd to the 356th from the N-terminus (a moiety of tyrosine-tyrosine-valine-phenylalanine-phenylalanine) of the natural TSHR is substituted with alanine (SEQ ID NOs: 8 and 21), in which 6 histidine residues are added to C terminal of amino acid residues (the 1st to the 415th from the N-terminus) of an extracellular domain moiety of the natural TSHR (SEQ ID NOs: 13 and 23), in which 42 amino acid residues containing the signal sequence of *baculovirus* gp 67 protein constituted by 38 amino acid residues are added to N terminal of and 6 histidine residues are added to C terminal of amino acid residues (the 21st to the 410th from the N-terminus) of an extracellular domain moiety of the natural TSHR (SEQ ID NOs: 17 and 24), and in which 42 amino acid residues containing the signal sequence of *baculovirus* gp 67 protein constituted by 38 amino acid residues are added to N terminal of and 6 histidine residues are added to C terminal of amino acid residues (the 21st to the 415th from the N-terminus) of an extracellular domain moiety of the natural TSHR (SEQ ID NOs: 18 and 25).
Figure 2B:
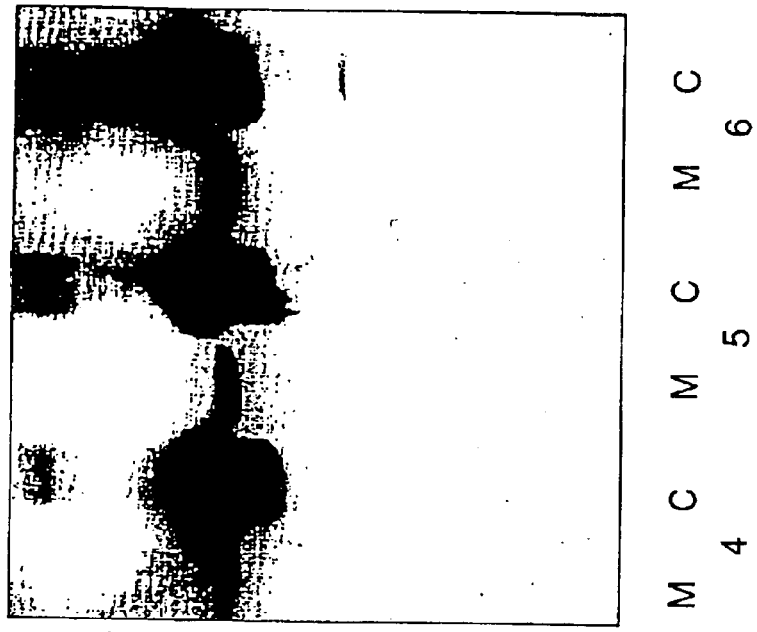
FIG. 2 shows a result of the detection of sTSHR expression in a culture supernatant fraction (M) and a cell extract fraction (C) of an insect cell infected with a recombinant virus into which cDNA encoding each of the 6 kinds of sTSHR shown in FIG. 1 was inserted, carried out by Western blotting using an anti-His$_6$ antibody.
Figure 2A:
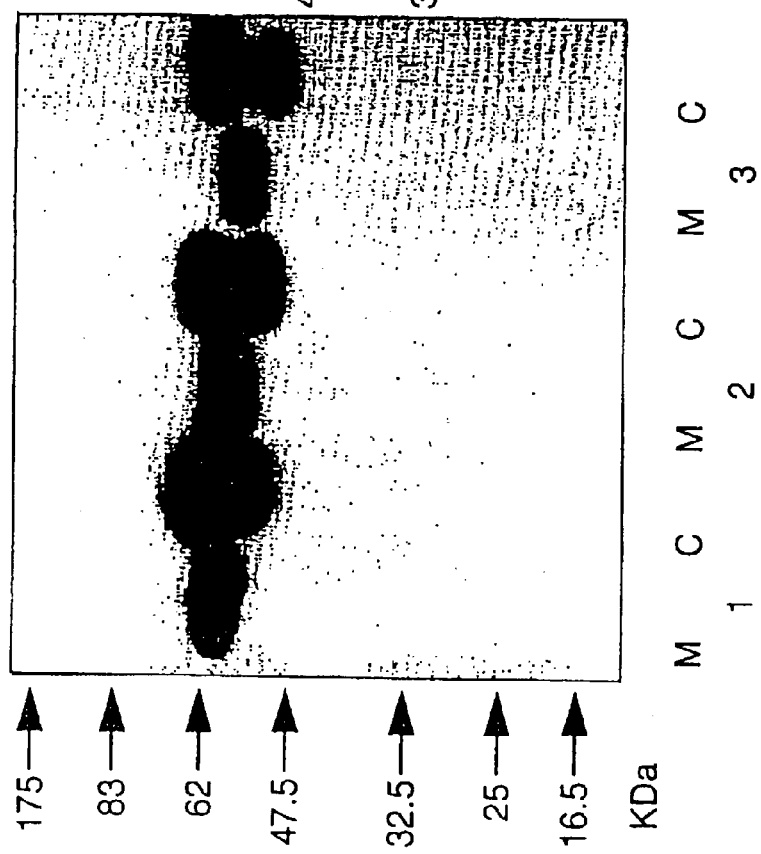

The sTSHR of the present invention can be produced using genetic recombination techniques. Among the techniques, a *baculovirus*-insect cell expression system can be exemplified as a particularly preferred expression system. The sTSHR keeping its higher-order structure can be obtained at a large amount by preparing a recombinant *baculovirus* in which a gene encoding sTSHR is inserted into the downstream of a strong *baculovirus* promoter, and infecting an insect cell with the thus prepared virus. Since the *baculovirus* DNA is as enormous as about 130 kDa, it is difficult to insert the sTSHR gene directly. Accordingly, in producing the sTSHR of the present invention, it is preferred to obtain a recombinant *baculovirus* by inserting the gene of interest into a transfer vector which can induce homologous recombination with the *baculovirus* DNA and then carrying out cotransfection of the vector together with *baculovirus* DNA into an insect cell to induce homologous recombination and formation of recombinant *baculovirus* DNA in the insect cell.

The gene (DNA) sequence encoding TSHR is already reported and generally known (e.g., *BBRC*, 165: 1184 (1989)). Thus, the transfer vector can be constructed by preparing a DNA sequence encoding its extracellular domain moiety based on such a report and then inserting it into the downstream of a strong *baculovirus* promoter, such as polyhedrin promoter or the like.

As the extracellular domain moiety of TSHR, a 415 amino acid residue moiety of the 1st to the 415th from the N-terminus and a 410 amino acid moiety of the 1st to the 410th from the N-terminus can be exemplified. Herein, a sequence of the 1st to the 20th from the N-terminus, so-called signal sequence, is present in sTSHR. According to the present invention, the finally produced sTSHR does not have this signal sequence, but when the vector or the like is constructed, a nucleotide sequence encoding the sequence of the 1st to the 20th from the N-terminus in natural TSHR is added. Also, this sequence may encode a signal sequence of *baculovirus* or an insect cell. For example, a signal sequence composed of 38 amino acid residues of an envelope protein (membrane protein), gp 67, of *baculovirus* can be used as the *baculovirus* signal sequence. According to the present invention, when a Hi five cell is preferably used as the insect cell for the production of sTSHR, it is preferred to use such a *baculovirus* signal sequence.

The sTSHR of the present invention may be subjected to mutation, such as deletion, substitution, insertion or addition, in comparison with the natural sequence, in an amino acid residue moiety of the 338th to the 366th from the N-terminus and/or in an amino acid residue moiety of the 352nd to the 356th from the N-terminus, so long as it is secretory and has reactivity with an anti-human thyroid stimulating hormone receptor autoantibody. More specifically, sTSHR in which an amino acid residue moiety of the 338th to the 366th is deleted or in which all of the amino acid residues of the 352nd to the 356th from the N-terminus are substituted with alanine can be exemplified.

In addition to these mutations, a mutation in which a gene encoding six histidine residues is inserted into the 3' side of the codons encoding the amino acid residues of the 410th to the 415th may be applied to the sTSHR of the present invention. The six histidine residues are useful when purification of sTSHR by metal chelate affinity chromatography or detection of sTSHR using an anti-His$_6$ antibody is carried out.

In order to express the extracellular domain moiety alone, a stop codon is inserted, for example, into the 3' side of a codon encoding the 410th amino acid from the N-terminus of TSHR or, when the gene encoding six histidine residues is inserted, into the 3' side of codons encoding the six histidine residues.

Cotransfection of the *baculovirus* DNA and transfer vector has no particular limitation and can be carried out in accordance with a usual method such as lipofection or the like.

The thus prepared sTSHR expression insect cell can be cultured in the usual way. Specifically, a static culture using a usual culturing apparatus and a mass culture using a usual culturing apparatus can be exemplified. In this case, the cell culture apparatus may be a spinner flask type or a tank type.

In an insect cell infected with the recombinant virus, expression of sTSHR becomes its peak during 48 to 72 hours after the infection by the action of a polyhedrin promoter existing in the recombinant virus. Since the sTSHR of the present invention is secreted from the insect cell into culture supernatant, it can be obtained by recovering the culture supernatant during 72 to 96 hours after infection with the recombinant virus and applying thereto usual protein purification techniques such as chromatography or the like. More specifically, it can be purified using lectin affinity chromatography having affinity for sugar chains. Also, when a gene mutagenized in such a manner that six histidine residues are added to the C-terminus of sTSHR as described above is used, sTSHR can also be purified by metal affinity chromatography using the six histidine residues.

Usual insect cells can be used as the host for expressing sTSHR. Among these, insect Hi five cells (e.g., Hi five cells manufactured by Invitrogen, Cat. No. B855-02, etc.) can be exemplified as particularly preferred insect cells. When insect cells such as the Hi five cells are used as the host cell, suspension culture can be made so that an effect of being able to culture using a convenient apparatus can be achieved.

As will be shown later in Examples, the sTSHR of the present invention produced by expressing a gene having a sequence encoding the *baculovirus* signal sequence on the 5' terminus using Hi five cells as insect cells is a particularly preferred sTSHR because it is secretory and, in addition to its reactivity with an anti-TSHR antibody, it shows excellent affinity for both of an antibody derived from patients with Graves' disease (hereinafter referred to as "TSAb") which stimulates thyroid gland through its binding to TSHR and another antibody (hereinafter referred to as "TSBAb") that blocks binding between TSH and TSHR.

Since the sTSHR of the present invention is a polypeptide, it can also be produced by chemically synthesizing partial fragments thereof according to the general techniques in the production of polypeptides, and then linking the partial fragments.

2. Reagent for Assaying Anti-TSHR Antibody Using sTSHR

The reagent of the present invention is, for example, a reagent containing sTSHR linked to a water-insoluble solid support. According to such a reagent, for example, an anti-TSHR autoantibody in human serum can be measured by linking it to a solid support via sTSHR and then using a labeled antibody for human immunoglobulin.

Examples of the useful solid support include plate shaped materials, such as a microtiter plate and the like, and beads shaped supports made of plastics, such as polystyrene, polypropylene and the like, and of inorganic substances, such as metal beads and the like.

Examples of the method for linking sTSHR to a solid support include a method in which sTSHR is physically absorbed by contacting it with a solid support (direct coating method) and a method in which it is linked via anti-TSHR antibody. Also, in the case of sTSHR in which six histidine residues are added to its C-terminus as described above, a method in which it is chelate-bonded with the histidine residues using a metal coating treated solid support or a method in which it is linked via anti-His$_6$ antibody for the histidine residues can also be used.

In an example of the direct coating method or chelate-binding method, about 100 µl of an sTSHR solution having a protein concentration of about 10 µg/ml is allowed to contact with a solid support and then to stand still overnight. Also, in an example of the method in which the linking is effected via an anti-TSHR antibody or an anti-His$_6$ antibody, the anti-TSHR antibody or anti-His$_6$ antibody is dissolved in a PBS solution to give a concentration of about 2 µg/ml, 100 µl of the solution is allowed to contact with a solid support and to stand still overnight, and then 100 µl of an sTSHR solution having a protein concentration of about 1 mg/ml is added thereto and allowed to stand still approximately overnight.

The reagent of the present invention for use in the measurement of anti-human thyroid stimulating hormone receptor is a reagent which can measure a physiological concentration of anti-TSHR autoantibody etc. contained in human serum accurately and quickly. This reagent is not particularly limited, so long as it contains sTSHR, and it may be a reagent for carrying out a competitive assay or a reagent for carrying out a sandwich assay. In addition, it may contain other reagents, which are required depending on the assay mode, such as wash water and a reagent for label detection. Furthermore, the reagent may contain carriers or diluents which are generally acceptable in this field.

Thus, the measurement of anti-TSHR antibody according to either a sandwich assay or a competitive assay by binding anti-TSHR antibody to a solid support via sTSHR. For example, when a sandwich assay is employed, it can be carried out using a labeled anti-human immunoglobulin antibody, by specifically binding the labeled anti-human immunoglobulin antibody to anti-TSHR antibody or the like linked to a solid support via sTSHR and detecting the label. Also, labeled TSH or labeled anti-TSHR antibody may be used in the case of a competitive assay. When labeled TSH is used, labeled TSH and anti-TSHR antibody are allowed to bind to sTSHR competitively, and the amount of anti-TSHR antibody is measured by detecting the labeled TSH bound to sTSHR. In this case, a TSH other than human origin, such as bovine origin, may be used as the TSH, but it is particularly preferred to use a human TSH or a TSH which is immunochemically identical thereto, such as a recombinant human TSH. When labeled anti-TSHR antibody is used, the amount of anti-TSHR antibody is measured by allowing the labeled anti-TSHR antibody and anti-TSHR autoantibody or the like in serum to bind to sTSHR competitively, and detecting the labeled TSH bound to sTSHR.

Examples of the label include a labeling substance usually used in the field of immunological measurement, such as a radioactive substance, a fluorescent substance, a luminescent substance, an enzyme typified by alkaline phosphatase or horseradish peroxidase, and the like.

3. Anti-TSHR Monoclonal Antibody

A monoclonal antibody for TSHR can be easily obtained by using the sTSHR of the present invention as the immunogen and employing usual screening techniques. Since the sTSHR of the present invention comprises an extracellular domain moiety of TSHR, this monoclonal antibody is an antibody which can also recognize natural TSHR expressed on human cells.

Accordingly, this monoclonal antibody has a possibility as an internal drug for diseases in which TSHR takes part, in addition to its use as the anti-TSHR autoantibody measuring reagent.

The present invention is a recombinant sTSHR which is effective in diagnosing autoimmune diseases. Its characteristic points are that it is secretory and has reactivity with an anti-TSHR autoantibody. Such a recombinant TSHR is not conventionally known and provided for the first time by the present invention. Since the sTSHR is secretory, particularly in the case of a fraction in which it is secreted into culture supernatant by a cell culture, a series of steps from its expression to purification can be conveniently carried out and, as a result, it exerts an effect of being able to produce it easily and at a large amount. When insect cells such as Hi five cells are used as the host cells particularly preferably, the mass production can be easily achieved by the effect peculiar to insect cells that suspension culturing can be carried out using a convenient apparatus.

Among members of the sTSHR of the present invention, a protein which is secreted into a culture supernatant fraction as described above does not require a treatment with a protease, such as trypsin or the like, in recovering it from a culture medium and can be purified by a means, such as centrifugation or the like, which has an extremely small possibility of having influences upon sTSHR. Thus, since disruption of host cells is not necessary in carrying out its purification, a possibility of being contaminated with impurities originated from the host cells can be reduced and, since the culture medium for insect cells does not require addition of protein components of serum-free medium or the like, another effect of being able to carry out high purity purification can also be achieved.

In addition to the above, the sTSHR of the present invention also has its affinity for TSH. As a result, various affinity purification means can be applied to its purification process, and it can be applied as a material for providing a novel reagent for use in the measurement of TSH and an anti-TSHR autoantibody.

The present invention is explained below in detail; however, the invention is not limited thereto.

Example 1

Isolation of sTSHR Gene:

A series of genetic recombination techniques in the examples were carried out with reference to the methods of Maniatis et al. (*Molecular Cloning, Cold Harbor Laboratory*, 1982).

Firstly, mRNA was isolated from human thyroid gland cells (excised thyroid gland tissue) by the guanidinium thiocyanate-phenol-chloroform extraction method. In this case, poly(A)+ RNA was prepared using oligo(dT) cellulose (Collaborative Research Inc., Type 2).

Human thyroid gland cell cDNA was synthesized by adding 5 μg of poly(A)+ RNA to a reaction solution containing a reverse transcriptase derived from moloney murine leukemia virus (GIBCO-BRL, 300 units), an RNase inhibitor derived from human placenta (manufactured by Wako Pure Chemical Industries, 15 units) and a random primer composed of 6 bases (0.5 μg), and carrying out the reaction at 37° C. for 60 minutes.

Example 2

Construction of a Transfer Vector Inserted with sTSHR cDNA Encoding Amino Acid Residues of the N-Terminus to the 410th of Natural TSHR:

The cDNA encoding an extracellular domain moiety of TSHR (410 amino acid residue moiety of the 1st to the 410th from the N-terminus) was amplified by PCR using the human thyroid gland cell cDNA as the template. A sense primer shTSHR-1 (SEQ ID NO: 1) in which an EcoRI recognition sequence (the 4th guanine to the 9th cytosine from the 5' end in SEQ ID NO: 1) and a three base Kozak sequence (the 10th adenine to the 12th cytosine from the 5' end in SEQ ID NO: 1) were fused to the 5' end of an oligonucleotide of 17 bases from the initiation codon of TSHR and an antisense primer ahTSHR-1 (SEQ ID NO: 2) in which an EcoRV recognition sequence (the 4th guanine to the 9th cytosine from the 5' end in SEQ ID NO: 2) was fused to the 5' end of an oligonucleotide which is complementary to the sequence moiety composed of 24 upstream bases from the codon corresponding to the 410th amino acid residue from the N-terminus of TSHR were used as the PCR primers, and PCR was carried out in a reaction solution containing DNA polymerase (Vent DNA polymerase, Biolabs).

Regarding preparation of double-stranded DNA encoding six continued histidine residues (histidine tag), two oligonucleotides (SEQ ID NOs: 3 and 4) were prepared in such a manner that, when a first oligonucleotide encoding the histidine tag and a stop codon is complementarily bonded to a second oligonucleotide complementary to the first oligonucleotide in a solution, certain sequences (N-terminus 3 bases and C-terminus 2 bases in SEQ ID NO: 3 and N-terminus 4 bases and C-terminus 3 bases in SEQ ID NO: 4) are formed in the N-terminus side of histidine tag when digested with StuI and in the C-terminus side when digested with NotI. Thereafter, these two oligonucleotides were mixed, heated and then returned to room temperature for complementary binding to prepare histidine tag-encoding double-stranded DNA which can be inserted into a plasmid having StuI and NotI recognition sequences.

Construction of an sTSHR recombinant transfer vector was carried out by treating a transfer vector pBac PAK9 (manufactured by Clontech) with StuI and NotI, inserting the histidine tag-encoding DNA into the vector which was subsequently treated with EcoRI and StuI, and then introducing the cDNA encoding the extracellular domain moiety of TSHR.

Structure of the thus constructed sTSHR and its corresponding nucleotide sequence and amino acid sequence are as shown in FIG. 1 (No. 1), SEQ ID NOs: 20 and 5, respectively.

Example 3

Preparation of a Transfer Vector Introduced with cDNA Encoding sTSHR Corresponding to the Amino Acid Residues of from the N-Terminus to the 410th of Natural TSHR, in which all of the Amino Acid Residues of the 352nd to the 356th from the N-Terminus are Substituted with Alanine:

Using the human thyroid gland cell cDNA obtained in Example 1 as the starting material, a transfer vector inserted with cDNA encoding sTSHR in which the amino acid residues of the 352nd to the 356th from the N-terminus of natural TSHR were substituted with alanine was prepared.

By employing the overlap elongation method (*GENE*, 77: 51–59 (1989)), cDNA encoding the receptor in which an amino acid residue moiety having high hydrophobicity (the 352nd to the 356th from the N-terminus) existing in the C-terminus of the extracellular domain moiety was substituted with alanine was prepared. Firstly, a sense primer shTSHR-2 (SEQ ID NO: 6) in which a DNA fragment encoding five alanine residues (16 bases of the 3' end in SEQ ID NO: 6) was fused to the 3' end of 18 bases encoding amino acid residues just before the amino acid moiety and an antisense primer ahTSHR-2 (SEQ ID NO: 7) in which an oligonucleotide having bases complementary to the five alanine residues (15 bases at the 3' end in SEQ ID NO: 7) was fused to the 5' end of 19 base oligonucleotide complementary to a DNA fragment encoding the amino acid residues just after the amino acid moiety were prepared, and, using the primers shTSHR-1 and ahTSHR-1 used in Example 2 and in respective combinations of shTSHR-1 with ahTSHR-2 and shTSHR-2 with ahTSHR-1, PCR amplification was separately carried out using the human thyroid gland cell cDNA as the template to prepare a cDNA fragment in which the cDNA encoding five alanine residues was fused to the 3' end side of the cDNA encoding an N-terminus amino acid residue moiety of the 1st to the 351st of natural TSHR and a cDNA fragment in which the cDNA encoding five alanine residues was fused to the 5' end side of the cDNA encoding an N-terminus amino acid residue moiety of the 357th to the 410th of natural TSHR. Since these two cDNA fragments have the same nucleotide sequence encoding five alanine residues on the 3' end or 5' end, cDNA encoding sTSHR in which a region of natural TSHR having high hydrophobicity, namely amino acid residues of the 352nd to the 356th from the N-terminus, were substituted with alanine residues was prepared by mixing them for complementary binding and then carrying out PCR amplification using shTSHR-1 and ahTSHR-1.

Thereafter, by the same procedure shown in Example 2, the thus prepared cDNA was treated with EcoRI and EcoRV and inserted into the histidine tag-attached transfer vector which had been treated with EcoRI and StuI in advance.

Structure of the sTSHR thus prepared in this example, in which amino acid residues of the 352nd to the 356th from the N-terminus of natural TSHR were substituted with alanine residues, and its corresponding nucleotide sequence and amino acid sequence are as shown in FIG. 1 (No. 2), SEQ ID NOs: 21 and 8, respectively.

Example 4
Preparation of a Transfer Vector Introduced with cDNA Encoding sTSHR Corresponding to the Amino Acid Residues of the N-Terminus to the 410th of Natural TSHR, in which an Amino Acid Residue Moiety of the 338th to the 366th from the N-Terminus is Deleted:

Using the human thyroid gland cell cDNA obtained in Example 1 as the starting material, a transfer vector introduced with cDNA encoding sTSHR in which an amino acid residue moiety of the 338th to the 366th from the N-terminus of natural TSHR was deleted was prepared.

By employing the overlap elongation method, cDNA encoding the receptor in which a region (the 338th to the 366th from the N-terminus) containing an amino acid residue moiety having high hydrophobic nature (the 352nd to the 356th from the N-terminus) existing in the C-terminus of the extracellular domain moiety was deleted was prepared. Firstly, a sense primer shTSHR-3 (SEQ ID NO: 9) and an antisense primer ahTSHR-3 (SEQ ID NO: 10) in which respective oligonucleotides encoding amino acid residues before and after the amino acid moiety were fused were prepared, and, using the primers shTSHR-1 and ahTSHR-1 used in Example 2 and in respective combinations of shTSHR-1 with ahTSHR-3 and shTSHR-3 with ahTSHR-1, PCR amplification was separately carried out using the human thyroid gland cell cDNA as the template, thereby preparing a cDNA fragment in which a moiety encoding amino acid residues of the 367th to the 370th from the N-terminus of natural TSHR was fused to the 3' end of a moiety encoding amino acid residues of the 1st to the 337th of the same receptor and a cDNA fragment in which a moiety encoding amino acid residues of the 334th to the 337th from the N-terminus of natural TSHR was fused to the 5' end side of a moiety encoding amino acid residues of the 334th to 337th of the same receptor. Since these two cDNA fragments have the same sequence portion having 24 bases, cDNA encoding sTSHR in which an amino acid residue moiety of the 338th to the 366th from the N-terminus of natural TSHR was deleted was prepared by mixing them for complementary binding and then carrying out PCR amplification using primers shTSHR-1 and ahTSHR-1.

Thereafter, by the same procedure shown in Example 2, the thus prepared cDNA was treated with EcoRI and EcoRV, and inserted into the histidine tag-attached transfer vector which had been treated with EcoRI and StuI in advance.

Structure of the sTSHR thus prepared in this example, in which amino acid residues of the 338th to the 366th from the N-terminus of natural TSHR were deleted, and its corresponding nucleotide sequence and amino acid sequence are as shown in FIG. 1 (No. 3), SEQ ID NOs: 22 and 11, respectively.

Example 5
Construction of a Transfer Vector Introduced with cDNA Encoding sTSHR Corresponding to the Amino Acid Residues of the N-Terminus to the 415th of Natural TSHR:

Using the human thyroid gland cell cDNA obtained in Example 1 as the starting material, construction of a transfer vector introduced with cDNA of sTSHR was carried out.

cDNA encoding an extracellular domain moiety (a moiety of 415 amino acid residues of the 1st to the 415th from the N-terminus) of TSHR was amplified by PCR using the human thyroid gland cell cDNA as the template.

The shTSHR-1 and an antisense primer ahTSHR-4 (SEQ ID NO: 12) complementary to a partial sequence of 20 bases upstream from a codon which corresponds to the 415th amino acid residue from the N-terminus of TSHR were used as the PCR primers for amplifying the moiety of 415 amino acid residues of the 1st to the 415th from the N-terminus of TSHR, and PCR was carried out in a reaction solution containing a DNA polymerase.

Thereafter, the thus prepared cDNA was treated with EcoRI and then, by the same procedure shown in Example 2, inserted into the histidine tag-attached transfer vector which had been treated with EcoRI and StuI in advance.

Structure of the thus constructed sTSHR and its corresponding nucleotide sequence and amino acid sequence are as shown in FIG. 1 (No. 4), SEQ ID NOs: 23 and 13, respectively.

Example 6
Preparation of a Transfer Vector Introduced with cDNA Encoding a Receptor in which the Signal Sequence of *Baculovirus* gp 67 Protein is Added to the N-Terminus of sTSHR Corresponding to Amino Acid Residues of the 21st to the 410th of Natural TSHR:

Using the thyroid gland cell cDNA prepared in Example 1 and another cDNA encoding the signal sequence of the *baculovirus* gp 67 protein as the starting materials, cDNA encoding a protein in which 42 amino acid residues. (SEQ ID NO: 19) containing the signal sequence of *baculovirus* gp 67 protein was added to the N-terminus of sTSHR corresponding to a moiety of the 21st to the 410th of natural TSHR was prepared.

The cDNA encoding the signal sequence of *baculovirus* gp 67 protein can be amplified by PCR using, for example, a DNA fragment into which the signal sequence of *baculovirus* gp 67 protein had been inserted (pAcGP67 A *baculovirus* transfer vector, PharMingen) as the template. A sense primer sGP67 (SEQ ID NO: 15) in which a BamHI recognition sequence (the 4th guanine to the 9th cytosine from the 5' end in SEQ ID NO: 15) and a 3 base Kozak sequence (10th adenine to the 12th cytosine from the 5' end in SEQ ID NO: 15) were fused to the 5'-terminus of an oligonucleotide of 20 bases from the initiation codon of the signal sequence of *baculovirus* gp 67 protein and an antisense primer aGP67 (SEQ ID NO: 16) in which an EcoRI recognition sequence (4th guanine to the 9th cytosine from the 5' end in SEQ ID NO: 16) was fused to the 5'-terminus of an oligonucleotide complementary to a partial sequence composed of 20 bases upstream from a codon corresponding to the 40th amino acid residue from the N-terminus of amino acid residues containing the signal sequence of *baculovirus* gp 67 protein were used as the PCR primers, and PCR was carried out in a reaction solution containing a DNA polymerase (Vent DNA polymerase, manufactured by Biolabs).

Thereafter, this cDNA was treated with BamHI and EcoRI and introduced into the histidine tag-attached transfer vector shown in Example 2, which had been treated with BamHI and EcoRI in advance.

The cDNA encoding an extracellular domain moiety (a moiety of 390 amino acid residues of the 21st to the 410th from the N-terminus) of TSHR was amplified by PCR using the human thyroid gland cell cDNA prepared in Example 1 as the template. A sense primer shTSHR-4 (SEQ ID NO: 14) in which an EcoRI recognition sequence (the 4th guanine to the 9th cytosine from the 5' end in SEQ ID NO: 14) was fused to the 5'-terminus of an oligonucleotide of 20 bases counting from a codon corresponding to the 21st amino acid residue of TSHR and the antisense primer ahTSHR-1 were used as the PCR primers, and PCR was carried out in a reaction solution containing a DNA polymerase (Vent DNA polymerase, manufactured by Biolabs).

Thereafter, this cDNA was treated with EcoRI and EcoRV and introduced between the *baculovirus* gp 67 protein signal sequence DNA and histidine tag DNA of the *baculovirus* gp 67 protein signal sequence- and histidine tag-attached transfer vector which had been treated with EcoRI and StuI in advance.

Figure 3:
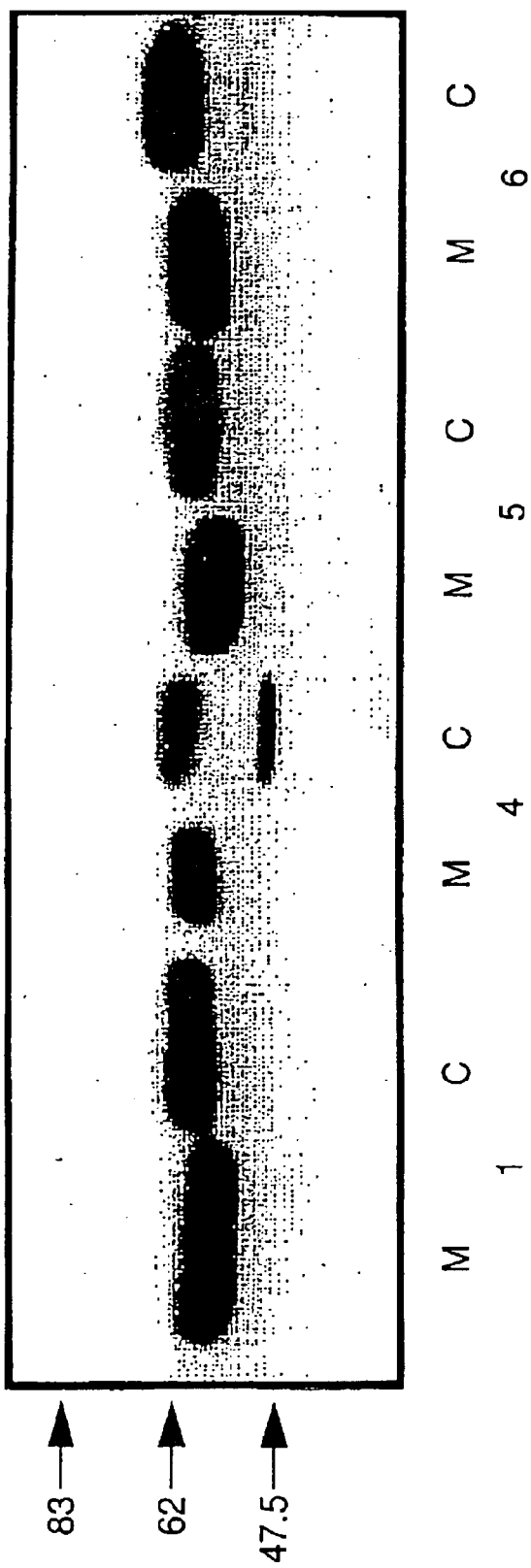
FIG. 3 shows a result of the detection of each of 4 kinds of sTSHR protein purified from a culture supernatant fraction (M) and a cell extract fraction (C) by metal affinity chromatography, carried out by Western blotting using an anti-His$_6$ antibody.

Structure of the cDNA encoding a receptor in which the signal sequence of *baculovirus* gp 67 protein was added to the N-terminus of sTSHR corresponding to amino acid residues of the 21st to the 410th of natural TSHR, and its nucleotide sequence and corresponding amino acid sequence are as shown in FIG. 1 (No. 5), SEQ ID NOs: 24 and 17, respectively.

Example 7

Preparation of a Transfer Vector Introduced with cDNA Encoding a Receptor in which the Signal Sequence of *Baculovirus* gp 67 Protein is Added to the N-Terminus of sTSHR Corresponding to Amino Acid Residues of the 21st to the 415th of Natural TSHR:

Using the thyroid gland cell cDNA prepared in Example 1 and another cDNA encoding the signal sequence of the *baculovirus* gp 67 protein as the starting materials, cDNA encoding a protein in which the signal sequence of *baculovirus* gp 67 protein was added to the N-terminus of sTSHR corresponding to a moiety of the 21st to the 415th from the N-terminus of natural TSHR was prepared.

The cDNA encoding the signal sequence of *baculovirus* gp 67 protein was prepared by the same method shown in Example 6 and introduced into the histidine tag-attached transfer vector.

The cDNA encoding an extracellular domain moiety (a moiety of 395 amino acid residues of the 21st to the 415th from the N-terminus) of TSHR was amplified by PCR using the human thyroid gland cell cDNA as the template. Using the sense primer shTSHR-4 and antisense primer ahTSHR-4 as the PCR primers, PCR was carried out in a reaction solution containing a DNA polymerase.

Thereafter, this cDNA was treated with EcoRI and introduced between the *baculovirus* gp 67 protein signal sequence DNA and histidine tag DNA of the *baculovirus* gp 67protein signal sequence- and histidine tag-attached transfer vector shown in Example 6, which had been treated with EcoRI and StuI in advance.

Structure of the cDNA encoding a receptor in which the signal sequence of *baculovirus* gp 67 protein was added to the N-terminus of sTSHR corresponding to amino acid residues of the 21st to 415th of natural TSHR, and its nucleotide sequence and corresponding amino acid sequence are as shown in FIG. 1 (No. 6), SEQ ID NOs: 25 and 18, respectively.

Example 8

Expression of sTSHR in Insect Cells:

Sf9 insect cells were subjected to cotransfection with the recombinant transfer vector and a viral DNA preparation (pBac PAK6; manufactured by Clontech) as Bsu36-digested expression vector and then cultured for 4 to 5 days to prepare a recombinant *baculovirus*. The sTSHR was expressed by infecting High five insect cells with the recombinant virus in a medium for insect cell use EX-CELL 400 (manufactured by JRH BIOSCIENCES) and culturing them at 27° C. for a period of from 72 to 96 hours.

The thus recovered culture supernatant was used as a culture supernatant fraction, and the recovered insect cells were disrupted with PBS containing 0.5% Triton-X to use the resulting soluble fraction as a soluble cell extract fraction.

Each of the culture supernatant fraction and soluble cell extract fraction was separated by subjecting it to an SDS-polyacrylamide gel (10%) electrophoresis under reducing condition and transferred on a PVDF membrane (Immobilon-P Transfer Membranes; manufactured by MILLIPORE). Next, the PVDF membrane was subjected to a blocking treatment using PBS containing 0.05% Tween 20 and 5% nonfat dry milk and then mixed with an anti-$His_6$ antibody (Anti-$His_6$-peroxidase; manufactured by Boehringer Mannheim) diluted to 1/500 with PBS, subsequently carrying out the reaction at room temperature for 1 hour.

After the reaction, the membrane was washed with PBS and allowed to react with a chemiluminescent horseradish peroxidase substrate (Renaissance; manufactured by DuPont NEN). The luminous reaction was visualized by exposing to an X-ray film (MEDICAL FILM; manufactured by KONICA) to confirm expression of sTSHR. The results are shown in FIG. 2.

As is evident from FIG. 2, when the sTSHR (1 in the drawing) composed of amino acid residues of the 1st to the 410th from the N-terminus of natural TSHR or the sTSHR (2 in the drawing) in which amino acid residues of the 352nd to the 356th of the same were substituted with alanine residues was expressed, a sTSHR of about 58 kDa was detected in the culture supernatant fraction, and a TSHR of about 63 or 49 kDa was detected in the intracellular fraction. On the other hand, when the sTSHR (3 in the drawing) in which amino acid residues of the 338th to the 366th from the N-terminus of the natural TSHR were deleted was expressed, a sTSHR of about 53 kDa was detected in the culture supernatant fraction, and a TSHR of about 58 or 43 kDa was detected in the intracellular fraction.

In addition, when the sTSHR (4 in the drawing) composed of amino acid residues of the 1st to the 415th from the N-terminus of natural TSHR or the sTSHR (5 or 6 in the drawing) in which the signal sequence of *baculovirus* gp 67 protein was added to the N-terminus of sTSHR encoding amino acid residues of the 21st to the 410th or from the 21st to the 415th was expressed, sTSHR of about 58 kDa was detected in the culture supernatant fraction, and TSHR of about 64 or 50 kDa was detected in the intracellular fraction.

Thus, sTSHR was secreted into the extracellular moiety at almost the same efficiency despite of the presence or absence of the hydrophobic region existing in the extracellular domain region of the natural TSHR, namely N-terminus amino acid residues of the 338th to the 366th or the 352nd to 356th, or of the difference in signal sequences.

Example 9

Purification of sTSHR Using a Metal Affinity Chromatography:

Each of the sTSHR samples described in Examples 2, 5, 6 and 7 (sTSHR samples of Nos. 1, 4, 5 and 6 shown in FIG. 1) was expressed by the method shown in Example 8, and each sTSHR in the culture supernatant fraction and cell extract fraction was purified by metal affinity chromatography. Regarding the purification of sTSHR from a culture supernatant fraction, the culture supernatant fraction was dialyzed overnight against PBS, NaCl and imidazole were added thereto to give final concentrations of 0.5 M and 20 mM, respectively, the mixture was applied to a nickel affinity column (His Trap; manufactured by Pharmacia Biotec.) and sTSHR was absorbed to the nickel affinity column using chelate binding of the six histidine residues added to the C-terminus of sTSHR with nickel. Elution of the absorbed sTSHR was carried out using PBS containing 250 mM imidazole as a competitor and 0.5 M NaCl. Regarding the purification of sTSHR from a cell extract fraction, the soluble cell extract fraction of Example 5 was mixed with NaCl and imidazole to give final concentrations of 0.5 M and 20 mM, respectively, followed by purification using the nickel affinity column in the same manner as the case of culture supernatant. The results are shown in FIG. 3. In FIG. 3, the sTSHR of No. 1, 4, 5 or 6 shown in FIG. 1, obtained after the purification, is detected with an anti-His$_6$ antibody by Western blotting.

It can be understood from FIG. 3 that sTSHR can be easily purified by metal affinity chromatography using the histidine tag added to the C-terminus of sTSHR.

Example 10

Purification of sTSHR Using Lectin Column:

Purification of sTSHR from the culture supernatant fraction and cell extract fraction in which the sTSHR described in Example 2 (sTSHR of No. 1 shown in FIG. 1) had been expressed by the method shown in Example 8 was carried out using the sugar added to the sTSHR, using a ConA column (HiTrap ConA; manufactured by Pharmacia Biotec.) having strong affinity for high-mannose and hybrid sugar chains and a lentil lectin column (HiTrap Lentil Lectin; manufactured by Pharmacia Biotec.) having affinity for sugar chains in which their reducing end sides are modified with fucose. Regarding the purification of sTSHR from the culture supernatant, the culture supernatant fraction of Example 8 was dialyzed overnight against PBS, mixed with NaCl, MnCl$_2$, CaCl$_2$ and Tris-HCl (pH 7.4) to give final concentrations of 0.5 M, 1 mM, 1 mM and 20 mM, respectively, and the mixture was applied to ConA column and Lentil Lectin column for binding of sTSHR to respective lectin columns. Elution of the sTSHR thus absorbed to the lectin columns was carried out using an eluting solution containing 1 M methyl-α-D-mannopyranoside as a competitor, 0.5 M NaCl and 20 mM Tris-HCl (pH 7.4).

Regarding the purification of sTSHR from the cell extract fraction, the soluble cell extract fraction of Example 8 was mixed with NaCl, MnCl$_2$, CaCl$_2$ and Tris-HCl (pH 7.4) to give final concentrations of 0.5 M, 1 mM, 1 mM and 20 mM, respectively, and the mixture was applied to the lectin columns in the same manner as the case of the culture supernatant fraction. The results are shown in FIG. 4.

As is evident from FIG. 4, in the case of the sTSHR of cell extract fraction (A in the drawing), a 49 kDa protein among proteins of 62 kDa and 49 kDa did not bind to ConA, but about several % of the high molecular weight side 62 kDa was bound to ConA. In addition, the sTSHR of cell extract fraction did not bind to lentil lectin. On the other hand, when the sTSHR of culture supernatant fraction (B in the drawing) was applied to ConA and lentil lectin, it bound to both of ConA and lentil lectin.

These results show that the 63 kDa sTSHR protein of cell extract fraction is a glycoprotein to which N-sugar chains, such as high-mannose and hybrid sugar chains, are added but their reducing end sides are not modified with fucose and that N-sugar chains are not added to the 49 kDa sTSHR protein of cell extract fraction. On the other hand, it is shown that N-sugar chains, such as high-mannose and hybrid sugar chains, having fucose-modified reducing end sides are added to the 58 kDa sTSHR protein of culture supernatant fraction.

Thus, it can be understood that the sTSHR of culture supernatant fraction can be purified using ConA or lentil lectin.

Example 11

Sugar Chains of sTSHR:

It has been reported that six N-sugar chain addition sites are present in the extracellular domain moiety of human TSHR and addition of O-sugar chains does not occur (*Endocrine Rev.*, 13: 61–76, (1992)) and that insect cells do not generally synthesize proteins having hybrid sugar chains. It has been reported also that sugar chains having different properties are added when the signal sequence of a *baculovirus* or insect cell is added to the extracellular domain moiety of human TSHR (*MCE*, 147: 133–142 (1999)). Accordingly, a culture supernatant fraction and a cell extract fraction in which the sTSHR described in Example 2 or 6 (the sTSHR of No. 1 or No. 5 in FIG. 1) had been expressed by the method described in Example 8 or 9 were subjected to the identification of sugar chains using sugar digestive enzymes. Sugar digestion was carried out by adding Endo F2 (Endoglycosidase F, rec.; manufactured by Boehringer Mannheim), Endo H (Endoglycosidase H; manufactured by Boehringer Mannheim), α-Mannosidase (α-Mannosidase suspension; manufactured by Wako Pure Chemical Industries) and PNGase (N-Glycosidase F, rec.; manufactured by Boehringer Mannheim), as sugar digestive enzymes specific for N-sugar chains, to a culture supernatant fraction or cell extract fraction containing sTSHR to which the human TSHR signal sequence described in Example 2 or the *baculovirus* gp 67 signal sequence described in Example 6 had been added.

After the digestion, examination of N-sugar chains was carried out by detecting the sugar-digested protein by Western blotting using an anti-His$_6$ antibody. Also, Endo F2 is an enzyme which digests hybrid sugar chains, Endo H digests high-mannose sugar chains and hybrid sugar chains, α-Mannosidase mainly digests α-1,2 and α-1,6 bonds of mannose existing in termini and PNGase digests all of N-sugar chains.

Figures 5A, 5B, 5C, 5D:
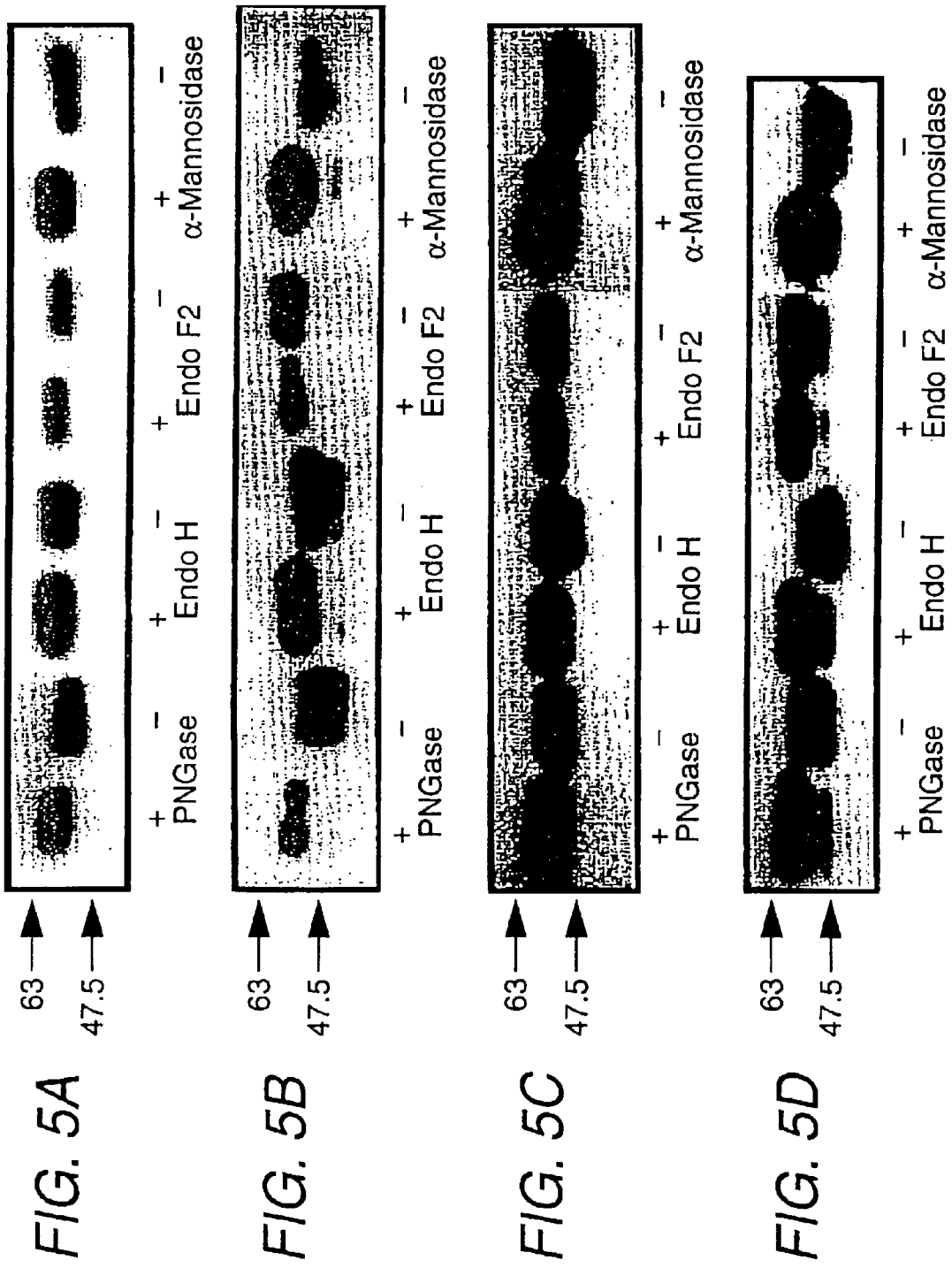
FIG. 5 shows a result in which sTSHR protein having the signal sequence of human TSHR purified from a culture supernatant fraction (A) and a cell extract fraction (B), and sTSHR protein having the signal sequence of *baculovirus* gp 67 protein purified from a culture supernatant fraction (c) and a cell extract fraction (D), by metal affinity chromatography, were digested with various enzymes and then detected by Western blotting using an anti-His$_6$ antibody.

Results on the sTSHR (No. 1 in FIG. 1) having human TSHR signal sequence and the sTSHR (No. 5 in FIG. 1) having *baculovirus* signal sequence, both contained in cell extract fractions, are shown in FIGS. 5B and 5D, respectively.

According to FIG. 5, the sTSHR having any of the signal sequences was not digested by the Endo F2 treatment but digested by the Endo H treatment, and its size was sharply reduced by the α-Mannosidase treatment, so that it is assumed that it has high-mannose sugar chains which have many mannose molecules on the sugar chain termini. On the other hand, both of the sTSHR having human TSHR signal sequence (FIG. 5A) and the sTSHR having *baculovirus* gp 67 signal sequence (FIG. 5C) were not digested by the Endo F2 and Endo H treatments, and their sizes were slightly reduced by the α-Mannosidase treatment, so that it is assumed that they have truncated high-mannose sugar chains having a small number of mannose molecules on the sugar chain termini. In addition, since the size of sTSHR proteins contained in the cell extract fraction and culture supernatant fraction was reduced to almost the same level by the PNGase treatment independent of the difference in signal sequences, it is assumed that they are proteins having the same amino acid residue moiety, merely having different sugar chains.

Since TSHR having truncated high-mannose sugar chains having a small number of mannose molecules on the sugar chain termini, like the case of the sTSHR of the present invention, is not known, this finding is novel.

Example 12

Influence of Glycosidase Inhibitors on the Secretion of sTSHR:

It has been reported recently that shifting of TSHR to the cell surface varies depending on the difference in sugar chains added to TSHR (*J. Biol. Chem.*, 273: 33423–33428 (1998)). Accordingly, in order to examine if addition of truncated high-mannose sugar chains is important for the secretion of sTSHR into cell culture supernatant using the sTSHR described in Example 6, Hi five insect cells were treated for 1 hour with 1 mM α-mannosidase I inhibitor 1-deoxymannojirimycin (dMM) or 10 μg/ml α-mannosidase II inhibitor Swansonine (SW), infected with the recombinant virus and cultured for 3 days, and then the culture supernatant was recovered to detect the presence or absence of the sTSHR secretion into the culture supernatant by Western blotting using an anti-His, antibody. The results are shown in FIG. 6.

Figure 6A:
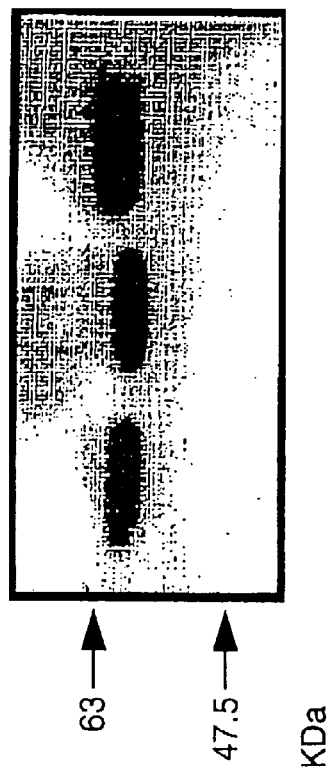
FIG. 6 shows a result (A) in which insect cells treated with a glycosidase inhibitor dMM or SW were infected with a recombinant virus, and the culture supernatants after 3 days of the infection were used for the detection in the presence or absence of sTSHR secretion into culture supernatant by Western blotting using an anti-His$_6$ antibody, and a result (B) in which the recovered culture supernatant (medium) was purified by metal affinity chromatography, sugar-digested with Endo H and then detected by Western blotting using an anti-His$_6$ antibody.
Figure 6B:
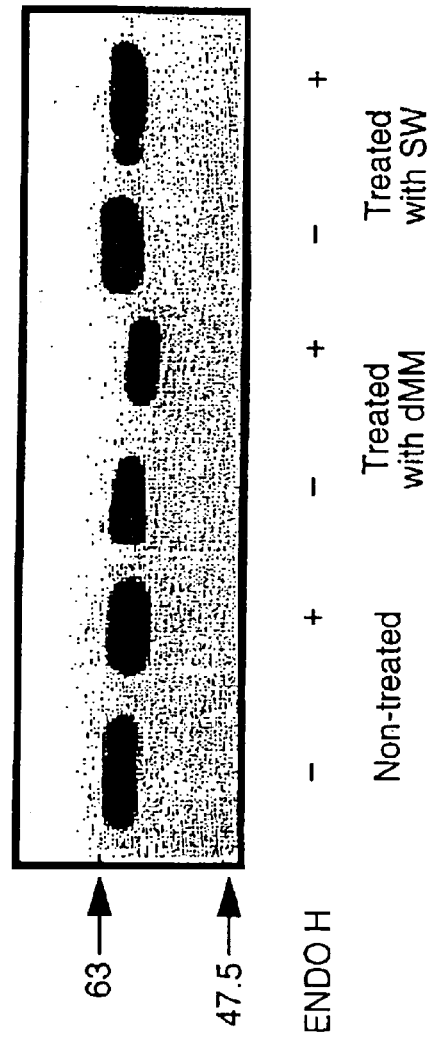

As is evident from FIG. 6, the sTSHR to which a high-mannose sugar chain $(GlcNac)_2(Man)_8$ had been added was expressed when dMM was used in the reaction, and the sTSHR to which another high-mannose sugar chain $(GlcNac)_2(Man)_5(GlcNac)$ had been added was expressed when SW was used. As is evident from FIG. 6A, the secretion of sTSHR was observed in the culture supernatant in each case of the reactions with dMM and SW. Also, according to FIG. 6B, when the recovered culture supernatant was purified by metal affinity chromatography, sugar-digested with Endo H and then detected by Western blotting using an anti-$His_6$ antibody, the sTSHR proteins expressed in the cells treated with dMM or SW were sugar-digested by Endo H, thus confirming the addition of high-mannose sugar chains thereto. Based on these results, it is considered that the sugar chains to be added are not necessarily truncated high-mannose sugar chains for the secretion of sTSHR into cell culture supernatant.

Example 13
Absorption Test of TBII in Serum from Patients with Graves' Disease or Hypothyroidism Patients Using sTSHR:

Antiserum of patients with Graves' disease or hypothyroidism patients (IgGs) inhibits binding of $^{125}$I-TSH to solubilized thyroid gland membrane (so-called TBII). An assay applying this action is commonly used for the diagnosis of patients with Graves' disease. The sTSHR having a human TSHR signal sequence described in Example 2 (No. 1 in FIG. 1) and the sTSHR to which baculovirus gp 67 signal sequence was added as described in Example 6 (No. 5 in FIG. 1) were expressed by the methods described in Examples 8 and 9, and their influences upon the action of patients' IgGs (sera from 6 cases of patients with Graves' disease having TSAb activity and 6 cases of hypothyroidism patients having TSBAb activity) to inhibit binding of TSH to thyroid gland membrane were examined.

Figure 7A:
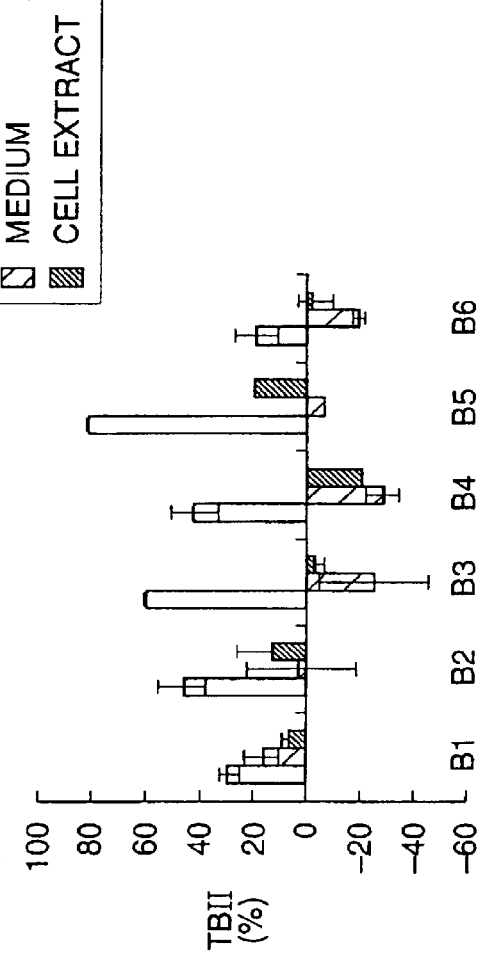
FIG. 7 shows a result of experimentation on whether or not TBII activity in sera from patients with Graves' disease or hypothyroidism patients can be inhibited by allowing the sera to react with sTSHR in advance. A1 to A6 correspond to sera from patients having TSAb activity, and B1 to B6 correspond to sera from patients having TSBAb activity.
Figure 7B:
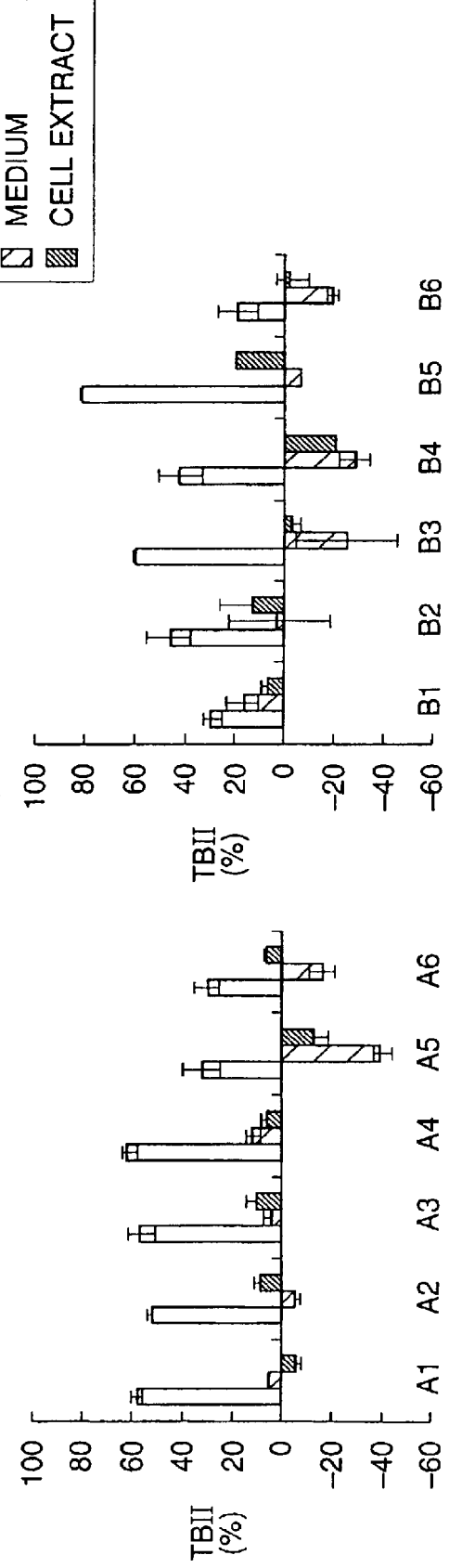
Figure 7C:
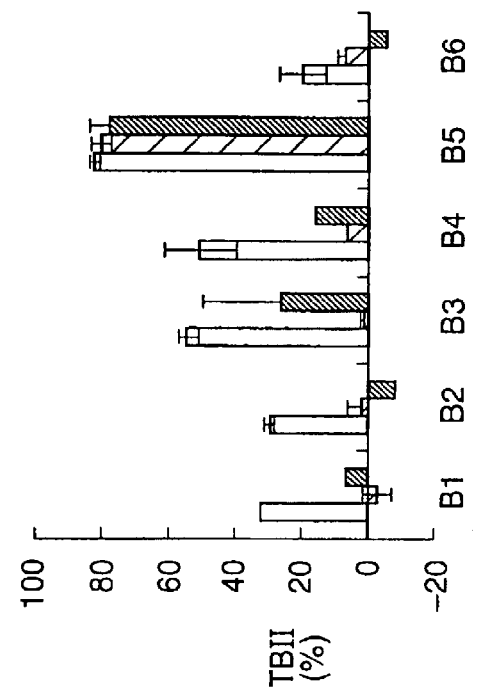
Figure 7D:
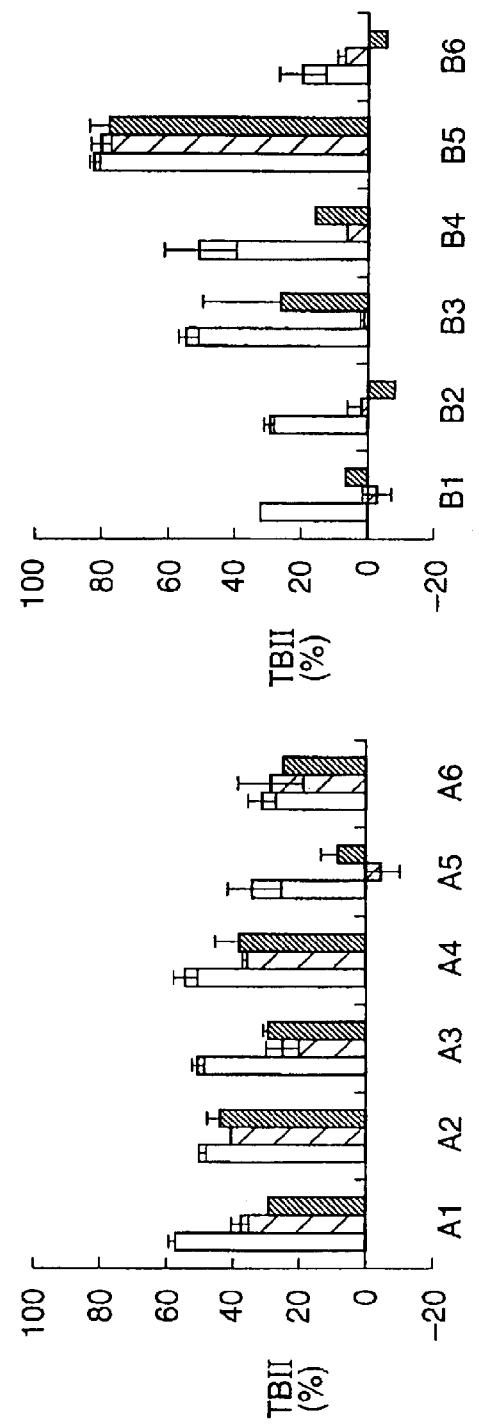

Each of the sTSHR samples was mixed in advance with each patient's serum for 1 hour, and TBII in the patient's serum was measured using a commercially available TBII assay kit (TRAb "Cosmic" II; manufactured by Cosmic Corporation). The sTSHR to which baculovirus gp 67 signal sequence was added (No. 5 in FIG. 1), contained in each of the culture supernatant fraction and cell extract fraction, completely absorbed TBII of the 6 cases of patients' sera having TSAb activity (FIG. 7A) and also absorbed TBII of the 6 cases of patients' sera having TSBAb activity (FIG. 7B). On the other hand, the sTSHR to which human TSHR signal sequence was added (No. 1 in FIG. 1) completely absorbed TBII of one case of patient's serum having TSAb activity, contained in each of the culture supernatant fraction and cell extract fraction, but the remaining five cases of serum showed low TBII absorption ratio (FIG. 7C). In the culture supernatant fraction and cell extract fraction, TBII was completely absorbed in 5 cases of serum having TSBAb activity excluding one case (FIG. 7D).

Thus, regarding the TBII of IgGs of patients with Graves' disease or hypothyroidism patients in the case of the sTSHR to which human TSHR signal sequence was added, absorption of TBII in serum having TSBAb activity was good, but absorption of TBII in serum having TSAb activity was not good. On the other hand, in the case of the sTSHR to which baculovirus signal sequence was added, absorption of TBII was good in both cases of sera having TSBAb activity and TSAb activity.

Example 14
Absorption Test of TSAb Activity in Serum from Patients with Graves' Disease Using sTSHR:

Serum of patients with Graves' disease (IgGs) having TSAb activity induces production of cyclic AMP (cAMP) through its binding to TSHR which is present in thyroid gland cells. Accordingly, the sTSHR having human TSHR signal sequence described in Example 2 (No. 1 in FIG. 1) and the sTSHR to which baculovirus gp 67 signal sequence had been added as described in Example 6 (No. 5 in FIG. 1) were expressed by the methods described in Examples 8 and 9, and their influences upon the cAMP production activity (TSAb activity) of thyroid gland cells by patients' IgGs (sera having TSAb activity of three Graves' disease cases) were examined.

Each of the sTSHR samples was mixed in advance with each patient's serum for 1 hour, and the TSAb activity in the patient's serum was measured using a commercially available TSAb assay kit (TSAb kit "Yamasa"; manufactured by Yamasa Shoyu). The results are shown in FIG. 8.

The sTSHR to which the baculovirus signal sequence had been added (No. 5 in FIG. 1), contained in each of the culture supernatant fraction and cell extract fraction, completely absorbed the TSAb activity of all of the 3 cases of sera (FIG. 8A). On the other hand, the sTSHR to which the human signal sequence was added (No. 1 in FIG. 1) completely absorbed the TSAb activity of only one case, contained in each of the culture supernatant fraction and cell extract fraction, but the remaining two cases of sera showed low TSAb activity absorption ratio (FIG. 8B).

Example 15
Absorption Test of TSBAb Activity in Serum from Hypothyroidism Patients Using sTSHR:

Antiserum (IgGs) having TSBAb activity in hypothyroidism patients inhibits production of cyclic AMP (cAMP) by TSHR which is present in thyroid gland cells. Accordingly, the sTSHR having human TSHR signal sequence described in Example 2 (No. 1 in FIG. 1) and the sTSHR to which baculovirus gp 67 signal sequence was added as described in Example 6 (No. 5 in FIG. 1) were expressed by the methods described in Examples 8 and 9, and their influences upon the action of the patients' IgGs (sera having TSBAb activity of three hypothyroidism cases) to inhibit TSHR activation were examined by the same procedure in Example 14.

Each of the sTSHR samples was mixed in advance with each patient's serum for 1 hour, and the TSBAb activity in the patient's serum was measured using the TSAb assay kit. The results are shown in FIG. 9.

Figure 9B:
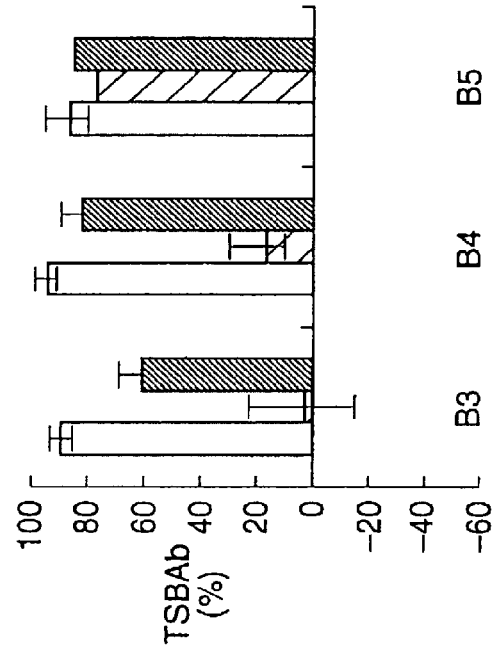
FIG. 9 shows a result of examination on whether or not TSBAb activity can be absorbed by allowing sera from patients with hypothyroidism having TSBAb activity to react with sTSHR in advance.
Figure 9A:
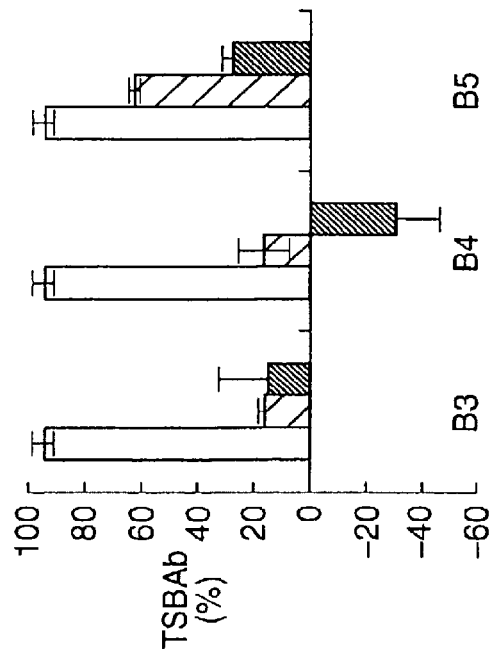
Figure 11:
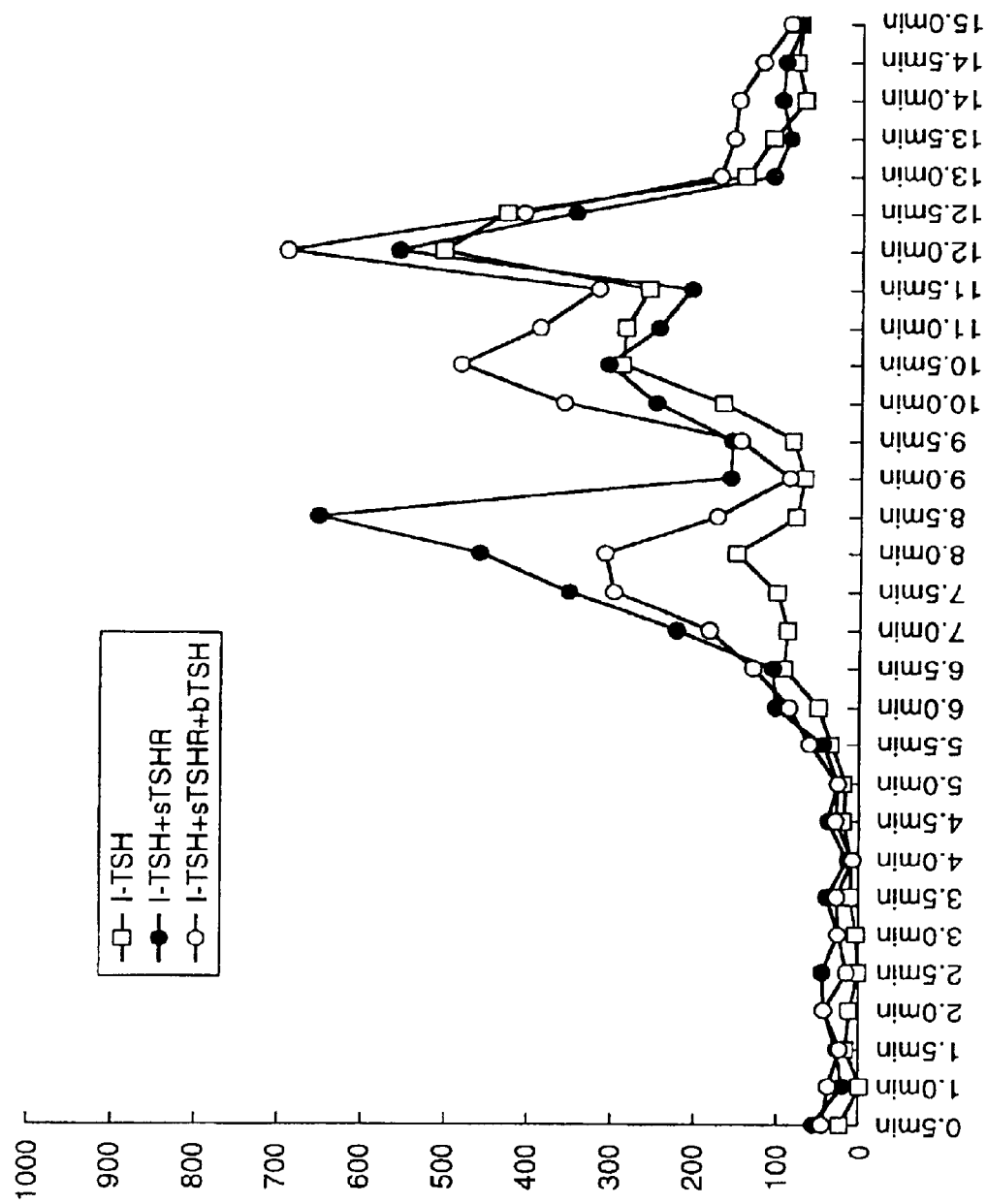
FIG. 11 is a graph (chromatogram) showing binding ability of sTSHR with TSH, wherein it shows a result on the sTSHR of No. 5 in FIG. 1 contained in a culture supernatant fraction. In the drawing, the open square indicates a result when $^{125}$I-TSH was separated, the black circle indicates a result when a mixed solution of $^{125}$I-TSH and sTSHR was separated and the open circle indicates a result when a mixed solution of $^{125}$I-TSH, sTSHR and bTSH was separated.

The sTSHR to which the baculovirus signal sequence had been added (No. 5 in FIG. 1), contained in each of the culture supernatant fraction and cell extract fraction, almost completely absorbed the TSBAb activity of all of the 3 cases of sera (FIG. 9A). On the other hand, in the case of the sTSHR having the human signal sequence (No. 1 in FIG. 1), the sTSHR contained in the culture supernatant fraction showed almost no absorption of the TSBAb activity in one case of the sera, but it completely absorbed the TSBAb activity in the remaining two cases of the sera (FIG. 9A). Also, the sTSHR contained in the cell extract fraction showed low TSBAb activity absorption ratio in all of the cases of sera (FIG. 9B).

Example 16
Detection of Anti-TSHR Autoantibody Using sTSHR:

The sTSHR to which *baculovirus* gp 67 signal sequence had been added as described in Example 6 (No. 5 in FIG. 1) was expressed by the methods described in Examples 8 and 9, linked through chelate binding to a nickel-immobilized 96 well plate (Ni—NTA H is Sorb Strips; manufactured by QIAGEN) and then allowed to react by adding sera from patients with Graves' disease (2 cases of sera from patients with Graves' disease having TSAb activity (A1 and A4) and 2 cases of sera from hypothyroidism patients having TSBAb activity (B2 and B3), 4 cases in total) or normal human sera (2 cases), which had been diluted 200 times with PBS.

After the reaction, these samples were allowed to react with an anti-human IgG antibody labeled with an alkaline phosphatase (anti-human IgG gamma chain alkaline phosphatase conjugate; manufactured by BIOSOURCE) which had been diluted 2,000 times with PBS, and the anti-TSHR antibody (IgG) bound to sTSHR was detected. The results are shown in FIG. 10.

As shown in FIG. 10, the normal human sera showed almost the same absorbance independent of whether or not the sTSHR was linked to the well. On the other hand, when the sera from patients with Graves' disease or hypothyroidism patients were used, significantly high absorbance was measured only in wells to which the sTSHR was linked.

Based on these results, it is obvious that the sTSHR of the present invention has reactivity with an anti-human thyroid stimulating hormone receptor antibody and is useful as a reagent for measuring an anti-TSHR autoantibody or a similar substance which is present in sera from patients with Graves' disease.

Example 17
Binding of sTSHR to bTSH:

The sTSHR described in Example 5, 6 or 7 (No. 4, 5 or 6 in FIG. 1) was expressed by the methods described in Examples 8 and 9 and used for the examination of its binding ability to bovine TSH (bTSH). Each sTSHR contained in the culture supernatant fraction or cell extract fraction was mixed with a solution prepared by mixing $^{125}$I-TSH or $^{125}$I-TSH with porcine TSHR, and the mixture was allowed to stand at 37° C. for 1 hour. Thereafter, the mixture was applied to a gel filtration column (G3000-XL, manufactured by Tosoh) and separated with an eluting solution containing 20 mM Tris-HCl (pH 7.4) and 50 mM NaCl. The eluate was recovered at 0.5 minute intervals, and the amount of $^{125}$I-TSH contained in each fraction was measured using a γ-counter. The results are shown in FIGS. 11 to 16.

In the chromatograms of FIGS. 11 to 16, the peak detected after 8 to 8.5 minutes indicates a complex of sTSHR with $^{125}$I-TSH, the peak detected after 10.5 minutes indicates $^{125}$I-TSH and the peak detected after 12 minutes indicates 125 I.

In the case of the sTSHR having the signal sequence of *baculovirus* gp 67 protein as described in Example 6 or 7 (No. 5 or 6 in FIG. 1), a peak indicating a complex of the receptor contained in the culture supernatant fraction with $^{125}$I-TSH was detected when they were mixed (FIGS. 11 and 13), but this peak was not detected when bTSH was added. These results revealed that the sTSHR of the present invention has the affinity for TSH.

Figure 12:
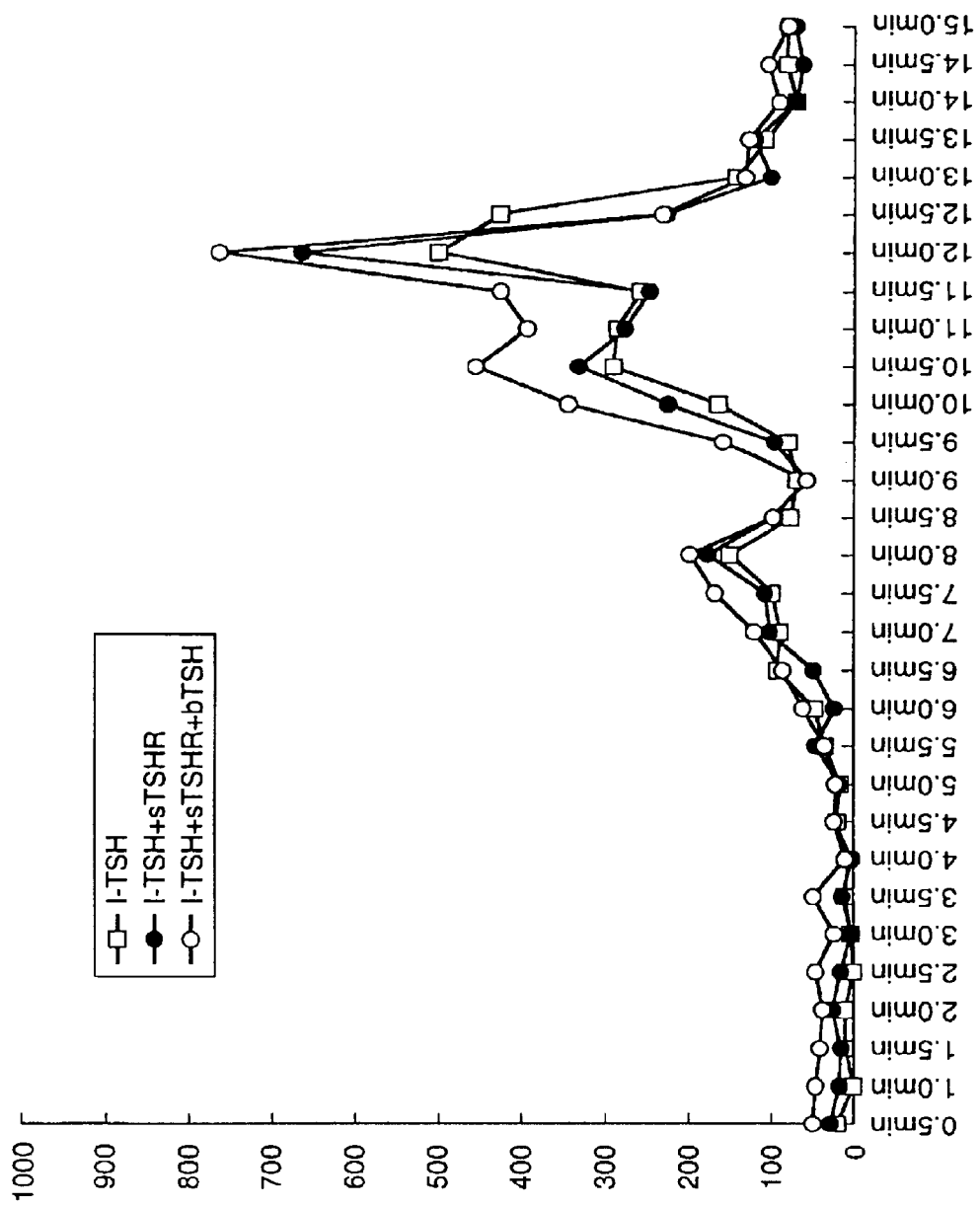
FIG. 12 is a graph (chromatogram) showing binding ability of sTSHR with TSH, wherein it shows a result on the sTSHR of No. 5 in FIG. 1 contained in a cell extract fraction. In the drawing, the open square indicates a result when $^{125}$I-TSH was separated, the black circle indicates a result when a mixed solution of $^{125}$I-TSH and sTSHR was separated and the open circle indicates a result when a mixed solution of $^{125}$I-TSH, sTSHR and bTSH was separated.
Figure 13:
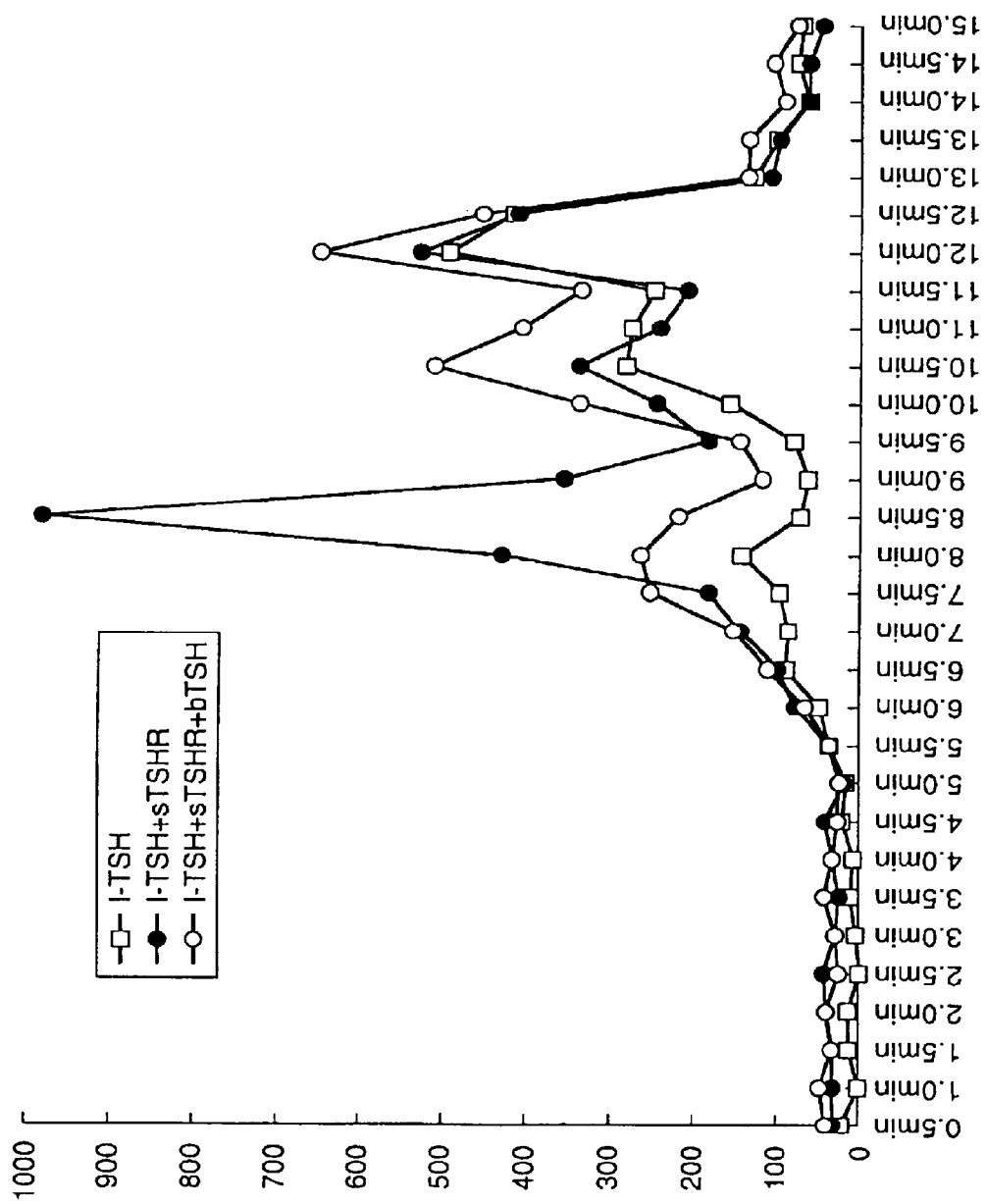
FIG. 13 is a graph (chromatogram) showing binding ability of sTSHR with TSH, wherein it shows a result on the sTSHR of No. 6 in FIG. 1 contained in a culture supernatant fraction. In the drawing, the open square indicates a result when $^{125}$I-TSH was separated, the black circle indicates a result when a mixed solution of $^{125}$I-TSH and sTSHR was separated and the open circle indicates a result when a mixed solution of $^{125}$I-TSH, sTSHR and bTSH was separated.
Figure 14:
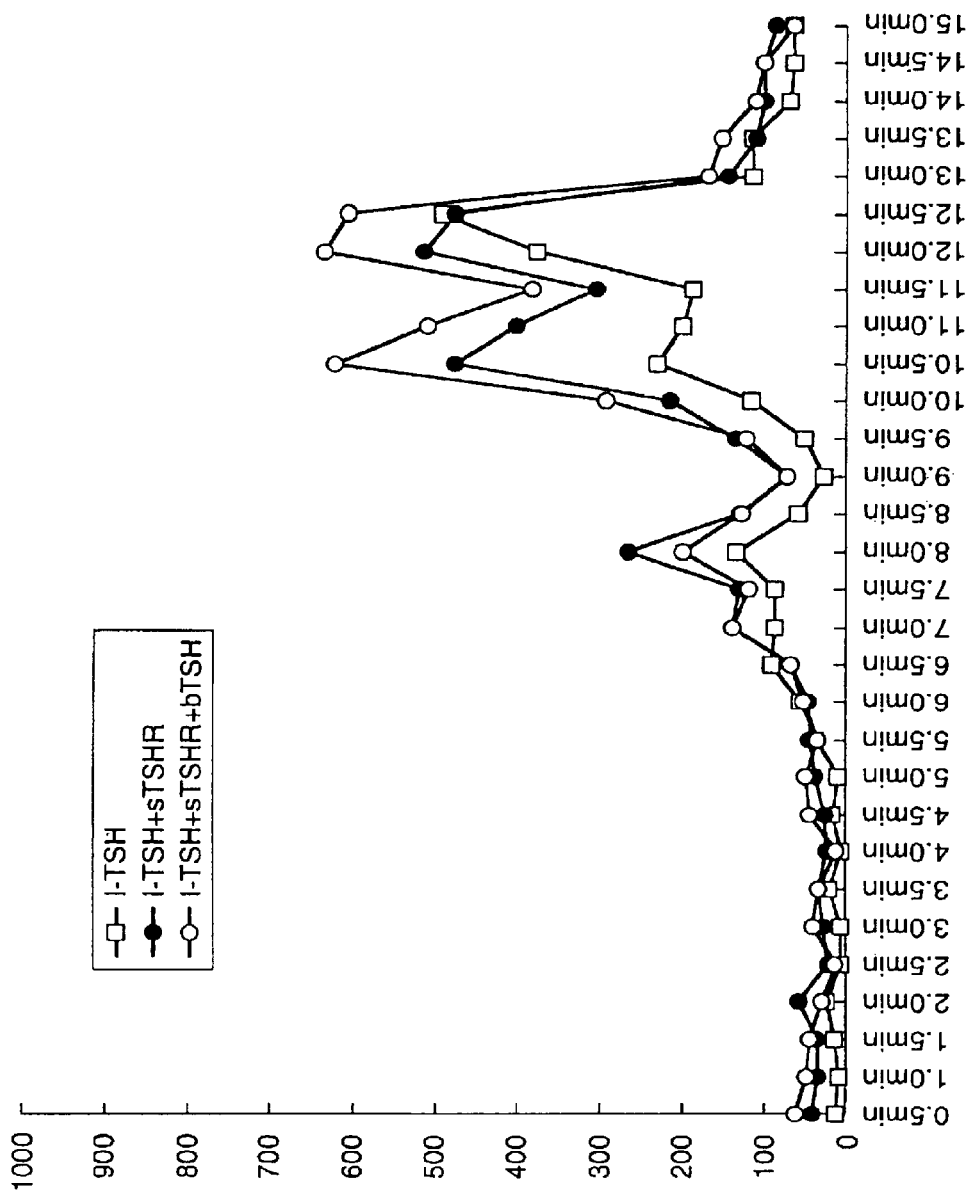
FIG. 14 is a graph (chromatogram) showing binding ability of sTSHR with TSH, wherein it shows a result on the sTSHR of No. 6 in FIG. 1 contained in a cell extract fraction. In the drawing, the open square indicates a result when 1251 TSH was separated, the black circle indicates a result when a mixed solution of $^{125}$I-TSH and sTSHR was separated and the open circle indicates a result when a mixed solution of $^{125}$I-TSH, sTSHR and bTSH was separated.
Figure 15:
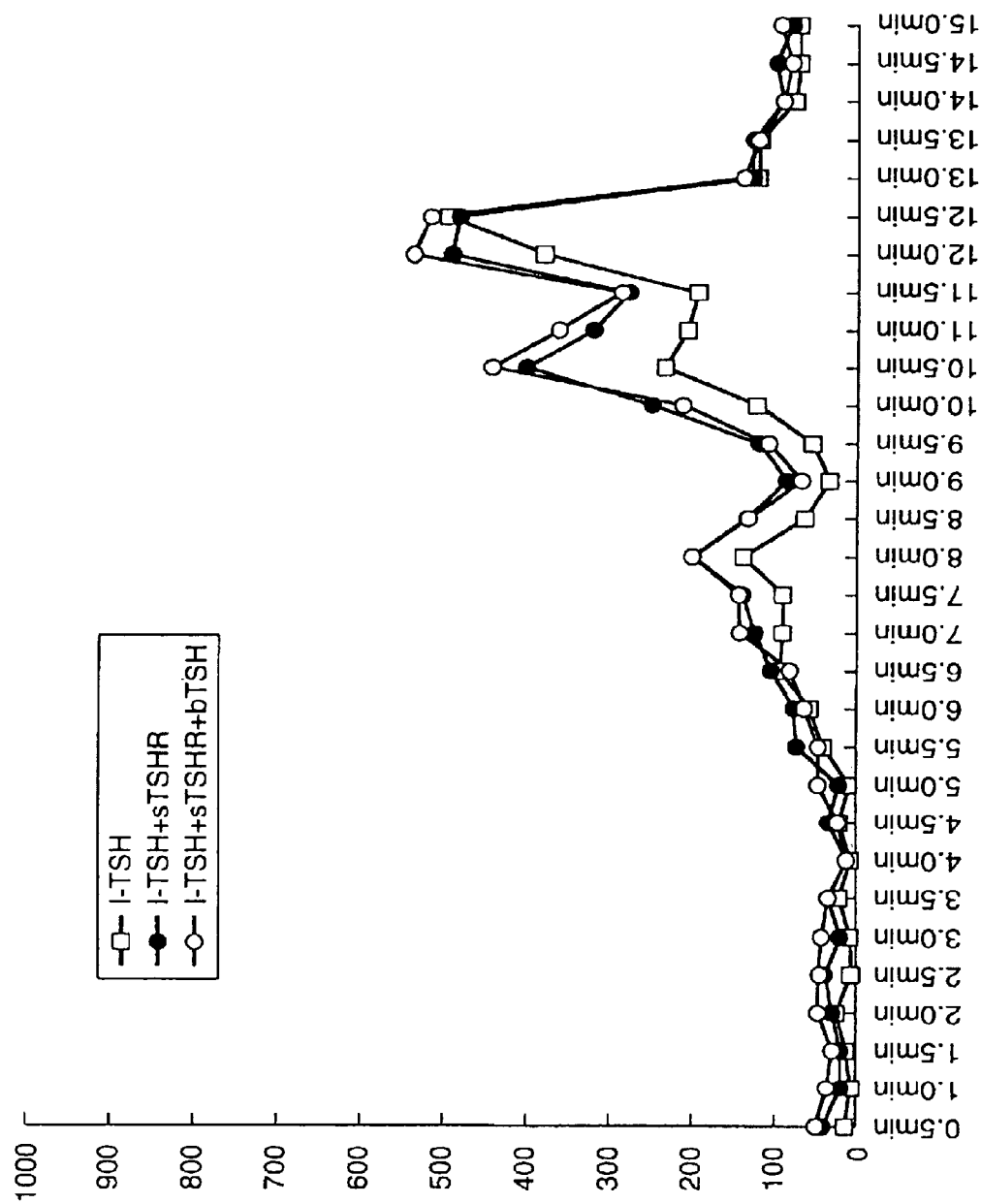
FIG. 15 is a graph (chromatogram) showing binding ability of sTSHR with TSH, wherein it shows a result on the sTSHR of No. 4 in FIG. 1 contained in a culture supernatant fraction. In the drawing, the open square indicates a result when $^{125}$I-TSH was separated, the black circle indicates a result when a mixed solution of $^{125}$I-TSH and sTSHR was separated and the open circle indicates a result when a mixed solution of $^{125}$I-TSH, sTSHR and bTSH was separated.
Figure 16:
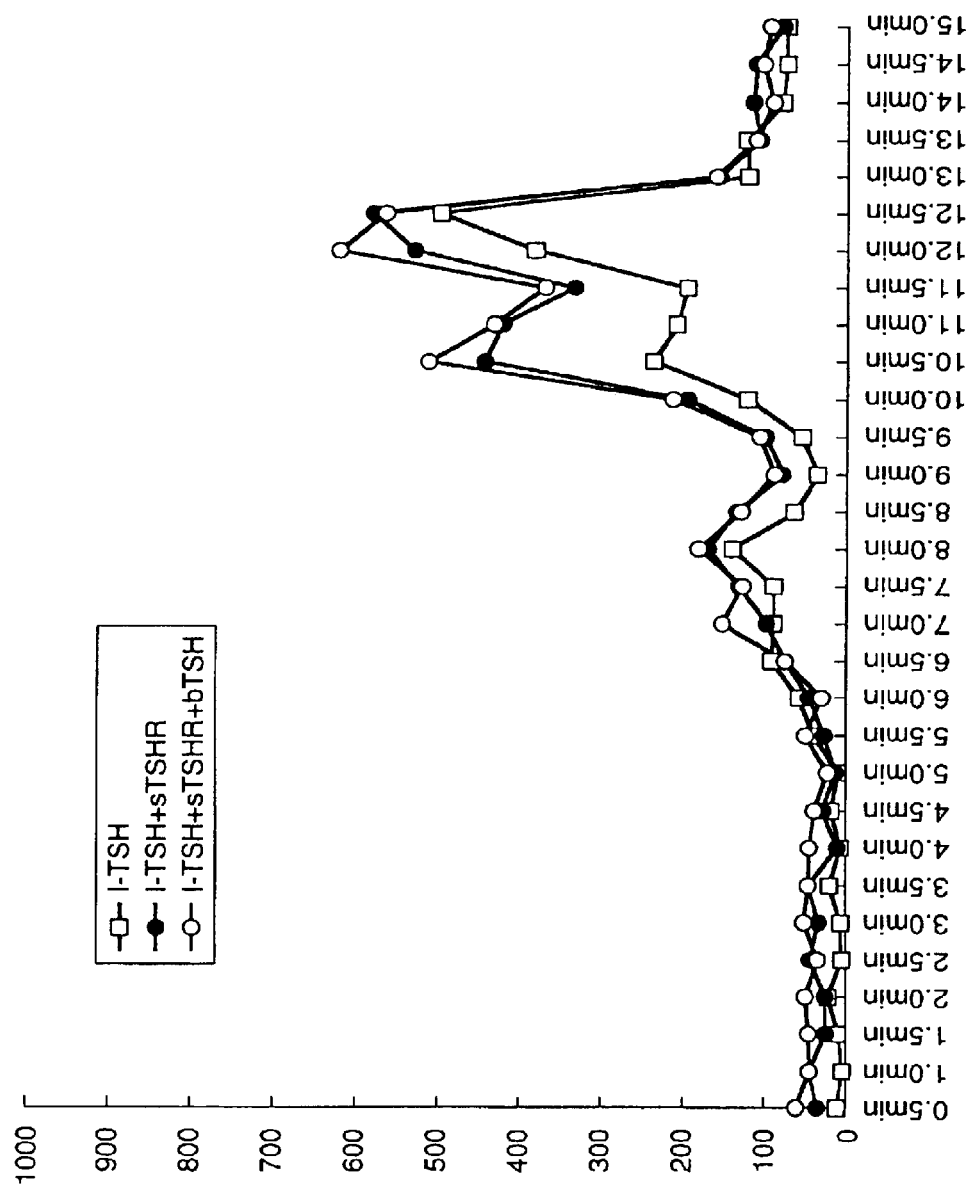
FIG. 16 is a graph (chromatogram) showing binding ability of sTSHR with TSH, wherein it shows a result on the sTSHR of No. 4 in FIG. 1 contained in a cell extract fraction. In the drawing, the open square indicates a result when $^{125}$I-TSH was separated, the black circle indicates a result when a mixed solution of $^{125}$I-TSH and sTSHR was separated and the open circle indicates a result when a mixed solution of $^{125}$I-TSH, sTSHR and bTSH was separated.

On the other hand, in the case of the sTSHR contained in the cell extract fraction, a peak similar to the above was not detected when it was mixed with $^{125}$I-TSH (FIGS. 12 and 14). Also, in the case of the sTSHR having human TSHR signal sequence as described in Example 5 (No. 4 in FIG. 1), contained in both of the culture supernatant fraction and cell extract fraction, a peak indicating a complex of sTSHR with $^{125}$I-TSH was not detected when it was mixed with $^{125}$I-TSH (FIGS. 15 and 16). It is evident from these results that the sTSHR which has the signal sequence of *baculovirus* gp 67 protein and is secreted into culture supernatant fraction has affinity for TSH.

This application is based on Japanese applications Nos. Hei 11-236983 filed on Aug. 24, 1999 and No. 2000-38214 filed on Feb. 10, 2000, the entire contents of which are incorporated hereinto by reference.

While the invention has been described in detail and with reference to specific embodiments thereof, it will be apparent to one skill in the art that various changes and modifications can be made therein without departing from the spirit and scope thereof.

What is claimed is:

1. A recombinant soluble human thyroid stimulating hormone receptor in free form, obtained by expressing in an insect cell a human thyroid stimulating hormone receptor gene with a nucleotide sequence encoding a signal sequence of *baculovirus* added to the 5' end of the human thyroid stimulating hormone receptor gene, comprising the signal sequence of *baculovirus* in connection with an extracellular domain moiety of a human thyroid stimulating hormone receptor, or a mutant thereof, being secreted to the extracellular space of the insect cell without artificial option, and having reactivity with an anti-human thyroid stimulating hormone receptor autoantibody, and having affinity for a thyroid stimulating hormone, and having N-sugar chains with fucose-modified reducing end sides.

2. The receptor according to claim 1, which comprises 395 amino acid residues of the 21st to the 415th from the N-terminus of a native human thyroid stimulating hormone receptor.

3. The receptor according to claim 1, which comprises 390 amino acid residues of the 21st to the 415th from the N-terminus of a native human thyroid stimulating hormone receptor.

4. The receptor according to claim 1, which comprises amino acid residues of the 338th to the 366th from the N-terminus of a native human thyroid stimulating hormone receptor which is subjected to at least one mutation selected from deletion, substitution, insertion and addition.

5. The receptor according to claim 1, which comprises amino acid residues of the 352nd to the 356th from the N-terminus of a native human thyroid stimulating hormone receptor which is subjected to at least one mutation selected from deletion, substitution, insertion and addition.

* * * * *